US006240306B1

(12) United States Patent
Rohrscheib et al.

(10) Patent No.: US 6,240,306 B1
(45) Date of Patent: May 29, 2001

(54) METHOD AND APPARATUS FOR NON-INVASIVE BLOOD ANALYTE MEASUREMENT WITH FLUID COMPARTMENT EQUILIBRATION

(75) Inventors: Mark Rohrscheib, Albuquerque, NM (US); Craig Gardner, Brooklyn, MA (US); Mark R. Robinson, Albuquerque, NM (US)

(73) Assignees: Rio Grande Medical Technologies, Inc.; University of New Mexico, both of Albuquerque, NM (US)

( * ) Notice: Subject to any disclaimer, the term of this patent is extended or adjusted under 35 U.S.C. 154(b) by 0 days.

(21) Appl. No.: 09/343,800

(22) Filed: Jun. 30, 1999

Related U.S. Application Data

(63) Continuation-in-part of application No. 09/174,812, filed on Oct. 19, 1998, which is a continuation-in-part of application No. 08/844,501, filed on Apr. 18, 1997, now Pat. No. 5,823,951, which is a continuation of application No. 08/512,940, filed on Aug. 5, 1995, now Pat. No. 5,655,530, which is a continuation-in-part of application No. 09/182,340, filed on Oct. 29, 1998.

(51) Int. Cl.[7] ........................................................ A61B 5/00
(52) U.S. Cl. ........................ 600/316; 600/310; 250/341.6
(58) Field of Search ..................................... 600/310, 322, 600/316, 323, 334, 473, 476; 250/339.03, 339.07, 341.1, 341.6, 341.8

(56) References Cited

U.S. PATENT DOCUMENTS

| 3,508,830 | 4/1970 | Hopkins et al. ................... 356/103 |
| 4,070,874 | 12/1991 | Barnes et al. . |
| 4,427,889 | 1/1984 | Muller ................................. 250/339 |
| 4,653,880 | 3/1987 | Sting et al. ......................... 350/620 |
| 4,655,225 | 4/1987 | Dhane et al. . |
| 4,661,706 | 4/1987 | Messereschmidt et al. ......... 250/341 |

(List continued on next page.)

FOREIGN PATENT DOCUMENTS

| 0 247 777 A1 | 12/1987 | (EP) . |
| 0 280 418 A1 | 8/1988 | (EP) . |
| 0 573 137 A2 | 12/1993 | (EP) . |
| WO 92/17765 | 10/1992 | (WO) . |
| WO 93/07801 | 9/1993 | (WO) . |

(List continued on next page.)

OTHER PUBLICATIONS

Bantle, John P. et al., "Glucose Measurement in Patients with Diabetes Mellitus with Dermal Interstitial Fluid," Copyright © 1997 by Mosby–Year Book, Inc., 9 pages.

Bleyer et al., "The Costs of Hospitalizations Due to Hemodialysis Access Management", Nephrology News & Issues, Jan. 1995, pp. 19–47.

(List continued on next page.)

Primary Examiner—Eric F. Winakur
(74) Attorney, Agent, or Firm—Crompton, Seager & Tufte, LLC

(57) ABSTRACT

A method and apparatus for non-invasively measuring the concentration of an analyte, particularly blood analyte in blood. The method utilizes spectrographic techniques in conjunction with equilibrating the concentration of the analyte between the vascular system fluid compartment of the test area and the other tissue fluid compartment. An improved optical interface between a sensor probe and a skin surface or tissue surface of the body containing the blood to be analyzed. Multiple readings during the equilibration period are taken and utilized to show the direction and rate of charge of concentration of the analyte in the blood which is useful in optimizing therapeutic response to the collected data.

39 Claims, 5 Drawing Sheets

U.S. PATENT DOCUMENTS

| | | | |
|---|---|---|---|
| 4,712,912 | | 12/1987 | Messerschmidt ..................... 356/73 |
| 4,714,341 | * | 12/1987 | Hamaguri et al. .................... 600/310 |
| 4,730,882 | | 3/1988 | Messerschmidt ................... 350/96.1 |
| 4,853,542 | | 8/1989 | Milsosevic et al. ................. 250/353 |
| 4,859,064 | | 8/1989 | Messerschmidt et al. .......... 356/446 |
| 4,882,492 | | 11/1989 | Schlager .............................. 250/346 |
| 4,975,581 | | 12/1990 | Robinson et al. ................... 250/339 |
| 5,007,423 | * | 4/1991 | Branstetter et al. ................ 600/334 |
| 5,015,100 | | 5/1991 | Doyle ................................... 356/445 |
| 5,019,715 | | 5/1991 | Sting et al. ........................... 250/571 |
| 5,028,787 | | 7/1991 | Rosenthal et al. ................... 250/341 |
| 5,051,602 | | 9/1991 | Sting et al. ........................... 250/571 |
| 5,158,082 | | 10/1992 | Jones . |
| 5,179,951 | | 1/1993 | Knudson . |
| 5,222,496 | | 6/1993 | Clarke et al. . |
| 5,225,678 | | 7/1993 | Messerschmidt .................... 250/339 |
| 5,230,702 | | 7/1993 | Lindsay et al. ........................... 604/4 |
| 5,237,178 | | 8/1993 | Rosenthal et al. ................... 250/341 |
| 5,267,563 | * | 12/1993 | Swedlow et al. .................... 600/323 |
| 5,299,570 | | 4/1994 | Hatschek . |
| 5,311,021 | | 5/1994 | Messerschmidt ............... 250/339.01 |
| 5,321,265 | | 6/1994 | Block .................................. 250/343 |
| 5,331,958 | | 7/1994 | Oppenheimer . |
| 5,348,003 | | 9/1994 | Caro . |
| 5,351,686 | | 10/1994 | Steuer et al. . |
| 5,355,880 | | 10/1994 | Thomas et al. . |
| 5,366,903 | | 11/1994 | Lundsgaard et al. ................ 436/165 |
| 5,372,135 | | 12/1994 | Mendelson et al. . |
| 5,379,764 | | 1/1995 | Barnes et al. . |
| 5,402,778 | | 4/1995 | Chance . |
| 5,405,315 | | 4/1995 | Khuri et al. ............................. 604/4 |
| 5,452,723 | | 9/1995 | Wu et al. . |
| 5,505,726 | | 4/1996 | Meserol .................................. 606/9 |
| 5,507,723 | | 4/1996 | Keshaviah ............................... 604/5 |
| 5,518,623 | | 5/1996 | Keshaviah et al. .................. 210/646 |
| 5,533,509 | | 7/1996 | Koashi et al. . |
| 5,636,633 | | 6/1997 | Messerschmidt et al. . |
| 5,655,530 | | 8/1997 | Messerschmidt . |
| 5,681,273 | | 10/1997 | Brown ..................................... 604/6 |
| 5,823,951 | | 10/1998 | Messerschmidt et al. ........... 600/322 |
| 5,827,181 | | 10/1998 | Dias et al. ............................ 600/322 |
| 5,830,132 | | 11/1998 | Robinson ............................. 600/310 |

FOREIGN PATENT DOCUMENTS

| | | |
|---|---|---|
| WO 98/03847 | 1/1998 | (WO) . |
| WO 99/55222 | 11/1999 | (WO) . |
| WO 00/22982 | 4/2000 | (WO) . |

OTHER PUBLICATIONS

Berkoben et al., "Vascular Access for Hemodialysis", *Clinical Dialysis*, published on or before Oct. 30, 1997, 20 pages.

Daugirdas et al., "Comparison of Methods to Predict the Equilibrated Kt/V (eKt/V) in the Hemo Study", National Institutes of Health, NIDDK, Bethesda, MD, Aug. 20, 1996.

Depner et al., "Clinical Measurement of Blood Flow in Hemodialysis Access Fistulae and Grafts by Ultrasound Dilution", from the Department of Nephrology, University of California, published on or before Oct. 30, 1997, 4 pages.

Jacobs et al., "A Disposable urea Sensor for Continuous Monitoring of Hemodialysis Efficiency", *ASAIO Journal*, 1993, pp. M353–M358.

Hakim et al., "Effect of Dose of Dialysis on Morbidity and Mortality", *American Journal of Kidney Diseases*, vol. 23, No. 5, May 1994, pp. 661–669.

Keshaviah et al., "On–line monitoring of the delivery of the hemodialysis prescription", *Pediatric Nephrology*, vol. 9, 1995, pp. S2–S8.

Krivitski, "Theory and Validation of Access Flow Measurement by Dilution Technique During Hemodialysis", *Kidney International*, vol. 48, 1995, pp. 244–250.

Marbach, "Measurement Techniques for IR Spectroscopic Blood Glucose Determination", 1993.

Ronco et al., "On–line urea monitoring: a further step towards adequate dialysis prescription and delivery", *Int'l Journal of Artificial Organs*, vol. 18, No. 9, 1995, pp. 534–543.

Service, F. John et al., Dermal Interstitial Glucose as an Indicator of Ambient Glycemia, *Diabetes Care*, vol. 20, No. 9, Sep. 1997, 9 pages.

Sherman, "Recirculation in the Hemodialysis Access", *Principles and Practice of Dialysis*, published on or before Oct. 30, 1997, 9 pages.

Sherman, "The Measurement of Dialysis Access Recirculation", *American Journal of Kidney Diseases*, vol. 22, No. 4, Oct. 1993, pp. 616–621.

Steuer et al., "A New Optical Technique for Monitoring Hematocrit and Circulating Blood Volume: Its Application in Renal Dialysis", *Dialysis & Transplantation*, vol. 22, No. 5, May 1993, 5 pages.

Webb, Paul, "Temperatures of Skin, Subcutaneous Tissue, Muscle and Core in Resting Men in Cold, Comfortable and Hot Conditions," *European Journal of Applied Physiology*, vol. 64 (1992) pp. 471–476.

Brochure entitled "Determination of Delivered Therapy Through Measurement of Effective Clearance", Fresenius USA, Dec. 1994, 1 page.

Brochure entitled "Improve the Clinical Outcome of Every Patient", In Line Diagnostics, published on or before Oct. 30, 1997, 2 pages.

* cited by examiner

METHOD AND APPARATUS FOR NON-INVASIVE BLOOD ANALYTE MEASUREMENT WITH FLUID COMPARTMENT EQUILIBRATION

CROSS REFERENCES TO CO-PENDING APPLICATIONS

This Application is a Continuation-in-Part of U.S. patent application Ser. No. 09/174,812, filed Oct. 19, 1998 entitled "Method for Non-Invasive Blood Analyte Measurement with Improved Optical Interface", which is a Continuation-in-Part of U.S. patent application Ser. No. 08/844,501, filed Apr. 18, 1997, entitled "Method for Non-Invasive Blood Analyte Measurement with Improved Optical Interface", now U.S. Pat. No. 5,823,951, issued Oct. 20, 1998, which is a continuation of U.S. patent application Ser. No. 08/512,940, filed Aug. 5, 1995, now U.S. Pat. No. 5,655,530, issued Aug. 12, 1997, all to the same assignee as the present application. This application is also a Continuation-in-Part of U.S. patent application Ser. No. 09/182,340, filed Oct. 29, 1998, entitled "Apparatus and Method for Determination of the Adequacy of Dialysis by Non-Invasive Near-Infrared Spectroscopy". The disclosure of each of the above referenced U.S. patent applications are expressly incorporated herein by reference.

TECHNICAL FIELD

The present invention relates generally to a non-invasive method and apparatus for measuring a blood analyte, particularly glucose, utilizing spectroscopic methods. More particularly, the method and apparatus incorporate means for equilibrating the concentration of specific analytes between tissue fluid compartments in a sample area, especially between blood and other tissue. The method and apparatus also includes an improved input optical interface for irradiating biological tissue with infrared energy having at least several wavelengths and an improved output optical interface for receiving non-absorbed infrared energy as a measure of differential absorption by the biological sample to determine an analyte concentration.

BACKGROUND OF THE INVENTION

The need and demand for an accurate, non-invasive method for determining blood glucose level in patients is well documented. Barnes et al. (U.S. Pat. No. 5,379,764) disclose the necessity for diabetics to frequently monitor glucose levels in their blood. It is further recognized that the more frequent the analysis, the less likely there will be large swings in glucose levels. These large swings are associated with the symptoms and complications of the disease, whose long-term effects can include heart disease, arteriosclerosis, blindness, stroke, hypertension, kidney failure, and premature death. As described below, several systems have been proposed for the non-invasive measurement of glucose in blood. However, despite these efforts a lancet cut into the finger is still necessary for all presently commercially available forms of home glucose monitoring. This is believed so compromising to the diabetic patient that the most effective use of any form of diabetic management is rarely achieved.

The various proposed non-invasive methods for determining blood glucose level, discussed individually below, generally utilize quantitative infrared spectroscopy as a theoretical basis for analysis. Infrared spectroscopy measures the electromagnetic radiation (0.7–25 $\mu$m) a substance absorbs at various wavelengths. Molecules do not maintain fixed positions with respect to each other, but vibrate back and forth about an average distance. Absorption of light at the appropriate energy causes the molecules to become excited to a higher vibration level. The excitation of the molecules to an excited state occurs only at certain discrete energy levels, which are characteristic for that particular molecule. The most primary vibrational states occur in the mid-infrared frequency region (i.e., 2.5–25 $\mu$m). However, non-invasive analyte determination in blood in this region is problematic, if not impossible, due to the absorption of the light by water. The problem is overcome through the use of shorter wavelengths of light which are not as attenuated by water. Overtones of the primary vibrational states exist at shorter wavelengths and enable quantitative determinations at these wavelengths.

It is known that glucose absorbs at multiple frequencies in both the mid- and near-infrared range. There are, however, other infrared active analytes in the blood which also absorb at similar frequencies. Due to the overlapping nature of these absorption bands, no single or specific frequency can be used for reliable non-invasive glucose measurement. Analysis of spectral data for glucose measurement thus requires evaluation of many spectral intensities over a wide spectral range to achieve the sensitivity, precision, accuracy, and reliability necessary for quantitative determination. In addition to overlapping absorption bands, measurement of glucose is further complicated by the fact that glucose is a minor component by weight in blood, and that the resulting spectral data may exhibit a non-linear response due to both the properties of the substance being examined and/or inherent non-linearities in optical instrumentation.

Another problem encountered in non-invasive skin based measurements of standard medical blood analytes in order to replace the need to draw blood from the patient has been the inherent differences between the concentration of a given analyte in the blood and the same analyte in the overall skin tissue water. Much of the work toward a replacement for blood drawing has been focused on the measurement of blood glucose in diabetic patients who must lance themselves four to five times per day in order to measure their capillary blood glucose concentration and adjust insulin therapy and meals. In the case of the infrared measurement, the beam "interrogates" a tissue volume that is largely water (70–80%).

However, blood, which is also approximately 80% water, makes up less than 10% of the tissue volume. Since glucose is not made, but only disposed of, in skin, all of the glucose in the water that bathes cells (interstitial fluid) and that is inside cells comes from the blood vessels. That is, blood glucose must move out of the blood vessels and into the surrounding interstitial water and then into cellular elements. This effect is, of course, time dependent as well as dependent upon the gradients, relative juxtaposition of the compartments, as well as the relative blood flow to the tissue. In short, the relationship between blood and tissue glucose concentration is very complex and variable even in a single subject. Thus, an integrated or summed measurement of total tissue water glucose concentration is often very different from the concentration of glucose in the small blood vessels that make up a fraction of the total tissue volume.

Glucose concentration measurement of interstitial fluid (the usually clear fluid that bathes all cells outside of blood vessels) as a surrogate for direct blood glucose concentration is problematic for some of the same reasons. Instead of measuring all compartments as with spectroscopic techniques, only one compartment is measured. Again, since glucose is only degraded in the skin (not manufactured), the interstitial space must be "filled" with glucose by the local blood vessels. This is analogous to a dye being slowly dripped into a glass of water, the faster the dye is dripped, the faster it reaches a high concentration or dark color throughout the total volume. As with any filling process, this is time dependent. Time lags between the concentration of glucose in interstitial fluid and blood have been documented ranging from zero to 60 minutes with an average lag of 20 minutes. Thus, the fact that the glucose must move between the tissue and blood causes errors in both interstitial space glucose and total tissue glucose concentration measurements.

When measurements of total tissue or interstitial glucose concentration and blood glucose concentration are made concurrently, the two are correlated, but the tissue glucose concentrations lag behind the blood levels. Blood or serum glucose concentrations must be delayed in order to overlay the interstitial or total glucose concentration. When blood glucose concentration is changing rapidly as might be expected in a diabetic after a meal high in simple carbohydrates (sugars) or after an insulin injection, the delay is more obvious and the difference between the blood and the other two measurements is most pronounced. The error between the blood measurement and the total or interstitial measurements is highest.

This presents obvious problems with respect to using the surrogate methods for monitoring and basing therapy in diabetic patients. Given the concentration difference, determining whether a given technique is working based on infrequent, discrete measurements is nearly impossible. Without continuous measurements, it is difficult to determine whether the patient's blood glucose is in a steady state condition or is in a flux; increasing or decreasing.

The worst case scenario in diabetic glucose management would be a quickly falling blood glucose concentration. Such a situation could result following a large insulin injection, unopposed by either glucose production in the liver or carbohydrate uptake from food in the gut. If a tissue measurement were made it would inappropriately report a level which is higher than the actual blood glucose concentration. Thus, the patient would be unaware of their actual low blood glucose level. The result of very low blood glucose concentrations (below 40 mg/dl, 2.2 mmol) is often coma and even brain damage or death if the patient is not discovered in time for medical intervention. Thus, improving the agreement between blood and tissue measurements is desired.

A further common element to non-invasive glucose measuring techniques is the necessity for an optical interface between the body portion at the point of measurement and the sensor element of the analytical instrument. Generally, the sensor element must include an input element or means for irradiating the sample point with infrared energy. The sensor element must further include an output element or means for measuring transmitted or reflected energy at various wavelengths resulting from irradiation through the input element.

Robinson et al. (U.S. Pat. No. 4,975,581) disclose a method and apparatus for measuring a characteristic of unknown value in a biological sample using infrared spectroscopy in conjunction with a multivariate model that is empirically derived from a set of spectra of biological samples of known characteristic values. The above-mentioned characteristic is generally the concentration of an analyte, such as glucose, but also may be any chemical or physical property of the sample. The method of Robinson et al. involves a two-step process that includes both calibration and prediction steps. In the calibration step, the infrared light is coupled to calibration samples of known characteristic values so that there is differential attenuation of at least several wavelengths of the infrared radiation as a function of the various components and analytes comprising the sample with known characteristic value. The infrared light is coupled to the sample by passing the light through the sample or by reflecting the light from the sample. Absorption of the infrared light by the sample causes intensity variations of the light that are a function of the wavelength of the light. The resulting intensity variations at the at least several wavelengths are measured for the set of calibration samples of known characteristic values. Original or transformed intensity variations are then empirically related to the known characteristic of the calibration samples using a multivariate algorithm to obtain a multivariate calibration model. In the prediction step, the infrared light is coupled to a sample of unknown characteristic value, and the calibration model is applied to the original or transformed intensity variations of the appropriate wavelengths of light measured from this unknown sample. The result of the prediction step is the estimated value of the characteristic of the unknown sample. The disclosure of Robinson et al. is incorporated herein by reference.

Several of the embodiments disclosed by Robinson et al. are non-invasive and incorporate an optical interface having a sensor element. As depicted in FIGS. 5 and 6 of Robinson et al., the optical interface includes first, an input element and second, an output element. The input element is an infrared light source or near infrared light source. The input element interface with the sample or body portion containing blood to be tested includes transmitting the light energy or propagating the light energy to the surface of the skin via the air. The output element includes a detector which receives the transmitted or reflected light energy. The output interface with the sample also includes propagating the transmitted or reflected light through the air from the skin.

Wall et al. in PCT Application WO 92/17765 disclose a method for measuring glucose within a blood sample utilizing a radiation beam having a wavelength in the bandwidth of 1500 nm to 1700 nm, and a reference radiation source emitting a radiation beam having a wavelength in the bandwidth of 1200 to 1400 nm. Both beams pass through a test medium of blood to a detector arranged to detect and produce an output signal dependent upon the intensity of radiation beams impinging thereon. Wall et al. disclose that it is preferred that the blood sample be heated because it was found that if the temperature of the blood in the cuvette was elevated to around 40° C., the amplitude of the light beam transmitted to a photodetector through the sample increased considerably. Wall et al. further state that for in vivo analysis, an electrically heated sleeve can be utilized as a finger-receiving cavity.

MacGregor et al. in PCT Application WO 93/07801 disclose a method and apparatus for determining non-invasively the presence and concentration of blood analytes such as glucose. The apparatus comprises a light source for producing a polychromatic light beam and means for modulating the polychromatic light beam, such that the modulation frequency is dependent upon the wavelength of light within the beam. The modulated light beam is caused to impinge upon a body part so that blood analytes interact with the light beam and perturb the spectral distribution of light within the beam. Spectral information is extracted from the resulting light beam by detecting the beam at a plurality of modulation frequencies. MacGregor et al. disclose that it is desirable to raise or lower the temperature of the body part to a constant temperature to minimize the variability in its spectral properties. It is disclosed that it is preferable to raise the body temperature, because the increasing temperature of the body part increases the amount of blood in the tissue and increases the strength of the pulsatile component of flow.

Robinson (U.S. Pat. No. 5,830,132) discloses a robust accurate non-invasive analyte monitor. The disclosure of Robinson is incorporated herein by reference. The method includes irradiating the tissue with infrared energy having at least several wavelengths in a given range of wavelengths so that there is differential absorption of at least some of the wavelengths by the tissue as a function of the wavelengths and the known characteristic, wherein the differential absorption causes intensity variations of the wavelengths incident from the tissue. The method further includes providing a first path through the tissue and a second path through the tissue, wherein the first path is optimized for a first sub-region of the range of wavelengths to maximize the differential absorption by at least some of the wavelengths in the first sub-region and then optimizing the second path for a second sub-region of the range to maximize the differential absorption by at least some of the wavelengths in the second sub-region. Robinson further discloses that the object of the invention is to measure blood analytes, therefore, maximizing the amount of blood in the tissue being irradiated is recognized as improving the measurement. The accuracy of non-invasive measurement is determined by its correlation to standard invasive blood measurements. To improve the stability and accuracy of the Robinson measurement, it is disclosed that a minimum sampling device should be thermostated so that the device does not act as a heat sink. It is further disclosed that the sampling device can be heated to an above normal tissue temperature to increase blood flow to the tissue area in contact with the device. The result is an increase in the vascular supply to the tissue and a corresponding increase in the blood content of the tissue. The end result of temperature regulation is taught as a reduction in spectral variation not associated with glucose and an improvement in measurement accuracy.

Barnes et al. (U.S. Pat. No. 5,379,764) disclose a spectrographic method for analyzing glucose concentration, wherein near infrared radiation is projected on a portion of the body, the radiation including a plurality of wavelengths, followed by sensing the resulting radiation emitted from the portion of the body as affected by the absorption of the body. The method disclosed includes pretreating the resulting data to minimize influences of offset and drift to obtain an expression of the magnitude of the sensed radiation as modified.

The sensor element disclosed by Barnes et al. includes a dual conductor fiber optic probe which is placed in contact or near contact with the skin of the body. The first conductor of the dual conductor fiber optic probe acts as an input element which transmits the near infrared radiation to the skin surface while in contact therewith. The second conductor fiber of the dual conductor probe acts as an output element which transmits the reflected energy or non-absorbed energy back to a spectrum analyzer. The optical interface between the sensor element and the skin is achieved by simply contacting the skin surface with the probe, and can include transmitting the light energy through air to the skin and through air back to the probe depending upon the degree of contact between the probe and skin. Irregularities in the skin surface and at the point of measurement will affect the degree of contact.

Dähne et al. (U.S. Pat. No. 4,655,225) disclose the employment of near infrared spectroscopy for non-invasively transmitting optical energy in the near infrared spectrum through a finger or earlobe of a subject. Also discussed is the use of near infrared energy diffusely reflected from deep within the tissues. Responses are derived at two different wavelengths to quantify glucose in the subject. One of the wavelengths is used to determine background absorption, while the other wavelength is used to determine glucose absorption.

The optical interface disclosed by Dähne et al. includes a sensor element having an input element which incorporates a directive light means which is transmitted through the air to the skin surface. The light energy which is transmitted or reflected from the body tissue as a measure of absorption is received by an output element. The interface for the output element includes transmitting the reflected or transmitted light energy through air to the detector elements.

Caro (U.S. Pat. No. 5,348,003) discloses the use of temporally-modulated electromagnetic energy at multiple wavelengths as the irradiating light energy. The derived wavelength dependence of the optical absorption per unit path length is compared with a calibration model to derive concentrations of an analyte in the medium.

The optical interface disclosed by Caro includes a sensor element having an input element, wherein the light energy is transmitted through a focusing means onto the skin surface. The focusing means may be near or in contact with the skin surface. The sensor element also includes an output element which includes optical collection means which may be in contact with the skin surface or near the skin surface to receive light energy which is transmitted through the tissue. Again, a portion of the light energy is propagated through air to the skin surface and back to the output element due to non-contact with the sensor and irregularities in the skin surface.

Problems with the optical interface between the tissue and the instrument have been recognized. In particular, optical interface problems associated with coupling light into and back out of the tissue were recognized by Ralf Marbach as published in a thesis entitled "MeBverfahren zur IR-spektroskopishen Blutglucose Bestimmung" (English translation "Measurement Techniques for IR Spectroscopic Blood Glucose Determination"), published in 1993.

Marbach states that the requirements of the optical accessory for measurement of the diffuse reflection of the lip are:

1) High optical "throughput" for the purpose of optimizing the S/N ratio of the spectra, and 2) Suppression of the insensitivity to Fresnel or specular reflection on the skin surface area.

The measurement accessory proposed by Marbach attempts to meet both requirements through the use of a hemispherical immersion lens. The lens is made out of a material which closely matches the refractive index of tissue, calcium fluoride. As stated by Marbach, the important advantages of the immersion lens for transcutaneous diffuse reflection measurements are the nearly complete matching of the refraction indices of $CaF_2$ and skin and the successful suppression of the Fresnel reflection.

Calcium fluoride, however is not an ideal index match to tissue, having an index of 1.42, relative to that of tissue, at approximately 1.38. Thus, an index mismatch occurs at the lens to tissue interface assuming complete contact between the lens and tissue. The optical efficiency of the sampling accessory is further compromised by the fact that the lens and the tissue will not make perfect optical contact due to roughness of the tissue. The result is a significant refractive index mismatch where the light is forced to travel from the lens (N=1.42) to air (N=1.0) to tissue (N=1.38). Thus, the inherent roughness of tissue results in small air gaps between the lens and the tissue, which decrease the optical throughput of the system, and subsequently compromise the performance of the measurement accessory.

The magnitude of the problem associated with refractive index mismatch is a complicated question. First, a fraction of light, which would otherwise be available for spectroscopic analysis of blood analytes, gets reflected at the mismatch boundary and returns to the input or collection optical system without interrogating the sample. The effect is governed by the Fresnel Equation:

$$R = \frac{(N'-N)^2}{(N'+N)^2}$$

For normally incident, randomly polarized light, where N and N' are the refractive indices of the two media. Solving for the air/$CaF_2$ interface gives an R=0.03, or a 3% reflection. This interface must be traversed twice, leading to a 6% reflected component which does not interrogate the sample. These interface mismatches are multiplicative. The fraction of light successfully entering the tissue then must be considered. In some regions of the spectrum, for instance, under a strong water band, almost all of the transmitted light gets absorbed by the tissue. The result is that this seemingly small reflected light component from the refractive index mismatch can virtually overwhelm and obscure the desired signal from the sample.

Finally, it is useful to consider the critical angle effect as light attempts to exit the tissue. Tissue is highly scattering and so a light ray which launches into tissue at normal incidence may exit the tissue at a high angle of incidence. If the coupling lens is not in intimate contact with the tissue, these high angle rays will be lost to total internal reflection. The equation which defines the critical angle, or the point of total internal reflection, is as follows:

$$\Theta_c = \sin^{-1}\left(\frac{N}{N'}\right)$$

When light is propagating through a higher index material like tissue (N'=1.38) and approaching an interface with lower refractive index like air (N=1.0), a critical angle of total internal reflection occurs. Light approaching such an interface at greater than the critical angle will not propagate into the rarer medium (air), but will totally internally reflect back into the tissue. For the aforementioned tissue/air interface, the critical angle is 46.4. No light steeper than this angle would escape. Intimate, optical contact is therefore essential to efficient light capture from tissue.

As detailed above, each of the prior art apparatus for non-invasively measuring glucose concentration utilize a sensor element. Each sensor element includes an input element and an output element. The optical interface between the input element, output element and the skin surface of the tissue to be analyzed in each apparatus is similar. In each instance, the input light energy is transmitted through air to the surface or potentially through air due to a gap in the contact surface between the input sensor and the skin surface. Likewise, the output sensor receives transmitted or reflected light energy via transmission through air to the output sensor, or potentially through a gap between the sensor element and the skin surface even though attempts are made to place the output sensor in contact with the skin. It is believed that the optical interfaces disclosed in the prior art affect the accuracy and consistency of the data acquired utilizing the prior art methods and apparatus. Thus, the accuracy of these methods for non-invasively measuring glucose are compromised.

Wu et al. (U.S. Pat. No. 5,452,723) disclose a method of spectrographic analysis of a tissue sample, which includes measuring the diffuse reflectance spectrum, as well as a second selected spectrum, such as fluorescence, and adjusting the spectrum with the reflectance spectrum. Wu et al. assert that this procedure reduces the sample-to-sample variability. Wu et al. disclose the use of an optical fiber as an input device that is bent at an acute angle so that incident light from the fiber impinges on an optically smooth surface of an optical coupling medium. The optical coupling medium is indexed matched to the tissue so that little or no specular reflection occurs at the interface between the catheter and the tissue. Wu et al. further disclose that the catheter can be used in contact or non-contact modes with the tissue. In contact mode, the end of the catheter is placed in direct contact with the tissue to accomplish index matched optical coupling. Thus, the optical coupling medium of Wu et al. is a solid end portion on the optical fiber. Wu et al. further disclose that the catheter can be used in a non-contact mode, wherein the gap left between the end of the catheter and the tissue can be filled with an index-matched fluid to prevent specular reflections. The only criteria disclosed throughout the Wu et al. specification for the fluid is that it is index matched to prevent specular reflections, which is only one aspect of an optimum optical interface for spectrographic analysis of an analyte in blood.

Accordingly, the need exists for a method and apparatus for non-invasively measuring glucose and other analyte concentrations in blood which accounts for or corrects problems associated with differences in analyte concentration in the various fluid compartments that comprise a tissue area or volume being tested. Further, there is a need for an apparatus and method to determine whether analyte concentrations are rising, falling or at equilibrium along with an indication of the rate of change in order to optimize treatment in response to the data. A preferred apparatus should incorporate an improved optical interface. The optical interface should produce consistent repeatable results so that the analyte concentration can be accurately calculated from a model such as that disclosed by Robinson et al. The optical interface should maximize both the input and output light energy from the source into the tissue and from the tissue back to the output sensor. The detrimental effects of gaps due to irregularities in the surface of the skin or the presence of other contaminants should be reduced or eliminated. Means should also be provided to guarantee that such optimized interface is achieved each time a user is coupled to the device for analysis.

The present invention addresses these needs as well as other problems associated with existing methods for non-invasively measuring glucose concentration in blood utilizing infrared spectroscopy and the optical interface associated therewith. The present invention also offers further advantages over the prior art and solves problems associated therewith.

SUMMARY OF THE INVENTION

The present invention is a method and apparatus for non-invasively measuring the concentration of an analyte, particularly glucose in blood, by analyzing human tissue. The method utilizes spectroscopic techniques in conjunction with an improved optical interface between a sensor probe and a skin surface or tissue surface of the body containing the tissue to be analyzed. The method and apparatus incorporate means for equilibrating the concentration of specific analytes between fluid compartments in a sample area.

The method for non-invasively measuring the concentration of glucose in blood includes first providing an apparatus for measuring infrared absorption by an analyte containing tissue. The apparatus includes generally three elements, an energy source, a sensor element, and a spectrum analyzer. The sensor element includes an input element and an output element. The input element is operatively connected to the energy source by a first means for transmitting infrared energy. The output element is operatively connected to the spectrum analyzer by a second means for transmitting infrared energy.

In preferred embodiments, the input element and output element comprise lens systems which focus the infrared light energy to and from the sample. In a preferred embodiment, the input element and output element comprise a single lens system which is utilized for both input of infrared light energy from the energy source and output of both specular and diffusely reflected light energy from the analyte-containing sample. Alternatively, the input element and output element can comprise two lens systems, placed on opposing sides of an analyte-containing sample, wherein light energy from the energy source is transmitted to the input element and light energy transmitted through the analyte-containing sample then passes through the output element to the spectrum analyzer.

The first means for transmitting infrared energy, in preferred embodiments, simply includes placing the infrared energy source proximate to the input element so that light energy from the source is transmitted via the air to the input element. Further, in preferred embodiments, the second means for transmitting infrared energy preferably includes a single mirror or system of mirrors which direct the light energy exiting the output element through the air to the spectrum analyzer.

In practicing the method of the present invention, an analyte containing tissue area is selected as the point of analysis. This area can include the skin surface on the finger, earlobe, forearm or any other skin surface. Preferably, the analyte-containing tissue in the area for sampling includes blood vessels near the surface and a relatively smooth, uncalloused skin surface. A preferred sample location is the underside of the forearm.

A quantity of an index-matching medium or fluid is then placed on the skin area to be analyzed. The index-matching fluid detailed herein is selected to optimize introduction of light into the tissue, reduce specular light and effectively get light out of the tissue. The medium or fluid preferably contains an additive which confirm proper coupling to the skin surface by a proper fluid, thus assuring the integrity of test data. It is preferred that the index-matching medium is non-toxic and has a spectral signature in the near infrared region which is minimal, and is thus minimally absorbing of light energy having wavelengths relevant to the analyte being measured. In preferred embodiments, the index-matching medium has a refractive index of about 1.38. Further, the refractive index of the medium should be constant throughout the composition. The composition of the index-matching medium is detailed below.

The sensor element, which includes the input element and the output element, is then placed in contact with the index-matching medium. Alternatively, the index-matching medium can be first placed on the sensor element, followed by placing the sensor element in contact with the skin with the index-matching medium disposed therebetween. In this way, the input element and output element are coupled to the analyte containing tissue or skin surface via the index-matching medium which eliminates the need for the light energy to propagate through air or pockets of air due to irregularities in the skin surface.

In preferred methods of the present invention, the method includes utilizing a means for equilibrating the concentration of an analyte or glucose between the vascular system or blood as a first fluid compartment and the other tissue of the sample area as a second fluid compartment. The means can include any method or apparatus which decreases the barrier to analyte transfer between fluid compartments, such as by causing an increase in the volume of blood or the rate of blood flow in the dermis and subcutaneous tissue. Importantly, the means increases the rate of equilibration of the analyte concentration in the blood relative to the analyte concentration in the surrounding interstitial tissue. In this way, the rate of delivery of glucose to or from the interstitial tissue and tissue as a whole is increased so that the result is a localized relative equilibrium between the blood or vascular compartments and the interstitial compartment. Thus, the means for equilibrating glucose or analyte concentration between fluid compartments allows the interstitial water compartment glucose concentration and tissue glucose concentration as a whole to follow the blood glucose concentration with little to no lag time, which results in greater agreement between blood measurements and non-invasive measurements.

The means for equilibrating the glucose or analyte concentration between the vascular system and the tissue can include local skin heating at the site of the analyte measurement for a sufficient time to achieve adequate equilibration. Alternatively, the method can include the use of rubrifractants or vasodilating agents such as nicotinic acid, methyl nicotinamide, minoxidil, nitroglycerin, histamine, capsaicin, or menthol which, when applied, increase local dermal blood flow equivalent to that induced by heating. Thus, in the preferred methods, means for equilibrating the glucose or analyte concentration between the vascular system and the tissue is first utilized prior to actual analysis of the analyte concentration so that the concentration of analyte or glucose in the tissue or interstitial fluid is first equilibrated with the concentration of analyte or glucose in the blood to give a more accurate overall concentration.

In another preferred embodiment of the present invention, the apparatus and method incorporate means for determining if the blood glucose or blood analyte concentration in the patient is increasing or decreasing. As detailed herein, the use of equilibration during a measurement session allows this determination. Both the direction and rate of change are monitored, which knowledge is extremely useful for planning therapy, whether it be insulin or caloric therapy such as prior to exercise, driving, sleeping or any activity that does not allow ready access to insulin or food supply for the diabetic patient.

In the method of this embodiment, an initial analyte concentration is determined based on the native state of the tissue. The tissue will, however, exhibit a disequilibrium between tissue and blood analyte or glucose concentrations if the analyte or glucose concentration in the blood has changed recently or is changing. In times of increasing glucose or other analyte level within the blood, the tissue analysis of the present invention generates a reading that is below the actual blood value due to the disequilibrium. Upon activation of the means for increasing the rate of equilibration of the analyte concentration between fluid compartments, the blood and tissue glucose or analyte concentrations rapidly equilibrate. Due to the short time period required, the tissue under analysis can remain in the measurement device of the present invention during the period of equilibration and multiple non-invasive tissue measurements can be made. Applicants have found that non-invasive measurements change rapidly and quickly equilibrate to the blood values. The rate of equilibration is also a measure of the rate at which the blood analyte concentration is changing. If blood analyte concentrations are decreasing, the non-invasive measurement would initially indicate a higher analyte concentration due to the lag concentration within the tissue. The disequilibrium can again be determined by multiple non-invasive measurements generated during the time of equilibration. The rate at which the non-invasive measurement drops to reach equilibrium is also indicative of the rate at which glucose or blood analyte concentrations are decreasing within the blood.

In analyzing for the concentration of glucose in the analyte containing tissue, light energy from the energy source is transmitted via the first means for transmitting infrared energy into the input element. The light energy is transmitted from the input element through the index-matching medium to the skin surface. Some of the light energy contacting the analyte-containing sample is differentially absorbed by the various components and analytes contained therein at various depths within the sample. Some of the light energy is also transmitted through the sample. However, a quantity of light energy is reflected back to the output element. In a preferred embodiment, the non-absorbed or non-transmitted light energy is reflected back to the output element upon propagating through the index-matching medium. This reflected light energy includes both diffusely reflected light energy and specularly reflected light energy. Specularly reflected light energy is that which reflects from the surface of the sample and contains little or no analyte information, while diffusely reflected light energy is that which reflects from deeper within the sample, wherein the analytes are present. In preferred embodiments, the specularly reflected light energy is separated from the diffusely reflected light energy. The non-absorbed diffusely reflected light energy is then transmitted via the second means for transmitting infrared energy to the spectrum analyzer. As detailed below, the spectrum analyzer preferably utilizes a computer to generate a prediction result utilizing the measured intensities, a calibration model, and a multivariate algorithm.

A preferred device for separating the specularly reflected light from the diffusely reflected light is a specular control device as disclosed in co-pending and commonly assigned application Ser. No. 08/513,094, filed on Aug. 9, 1995, and entitled "Improved Diffuse Reflectance Monitoring Apparatus", now U.S. Pat. No. 5,636,633, issued Jun. 10, 1997. The above patent disclosure is hereby incorporated by reference.

In an alternative embodiment, the input element is placed in contact with a first quantity of index-matching medium on a first skin surface, while the output element is placed in contact with a second quantity of index-matching medium on an opposing skin surface. Alternatively, the index-matching medium can be placed on the input and output elements prior to skin contact so that the medium is disposed between the elements and the skin surface during measurement. With this alternative embodiment, the light energy propagated through the input element and first quantity of index-matching medium is differentially absorbed by the analyte containing tissue or reflected therefrom, while a quantity of the light energy at various wavelengths is transmitted through the analyte containing tissue to the opposing or second skin surface. From the second skin surface, the non-absorbed light energy is propagated through the second quantity of index-matching medium to the output element with subsequent propagation to the spectrum analyzer for calculation of the analyte concentration.

The index-matching medium of the present invention is a key to the improved accuracy and repeatability of the method described above. The index-matching medium is preferably a composition containing chlorofluorocarbons. The composition can also contain perfluorocarbons. One preferred index-matching medium is a fluorinated-chloronated hydrocarbon polymer oil manufactured by Oxidant Chemical under the tradename FLUOROLUBE.

It has been found that the index-matching mediums of the present invention optimize the analysis of a blood analyte in human tissue by effectively introducing light into the tissue, reducing specular light, and effectively getting light back out of the tissue, which has been diffusely reflected from analyte-containing areas of the tissue, back to the output device. This requires selection of an index-matching medium that not only has the proper refractive index, but also has minimal absorption of infrared energy at wavelengths which are relevant to the measurement of the analyte of interest. Therefore, a preferred index-matching medium of the present invention is minimally or essentially non absorbing of light energy in the near infrared range of the spectrum.

In preferred embodiments, the index-matching medium of the present invention also includes a diagnostic additive. The diagnostic additive in the index-matching fluid allows a determination of the height of the fluid layer and/or provides a wavelength calibration for the instrument. These additives allow for assessment of the quality of the lens/tissue interface and assessment of instrument performance each time an individual is tested utilizing the apparatus of the present invention. The diagnostic additive can account for about 0.2% to about 20% by weight of the overall fluid. In an alternative embodiment, the index-matching medium and the diagnostic additive can comprise the same compound which serves both functions.

The index-matching medium of the present invention can also include physiological additives which enhance or alter the physiology of the tissue to be analyzed. In particular, preferred physiological additives include vasodilating agents which decrease the equilibration time between capillary blood glucose concentration and skin interstitial fluid glucose concentrations to provide a more accurate blood glucose number. The physiological additives can account for about 0.2% to about 20% by weight of the overall fluid.

The compound can also contain other additives such as a hydrophilic additive like isopropyl alcohol. The hydrophilic compound is believed to tie up the moisture in the skin surface to improve the interface between the fluid and skin. Further, the index-matching medium can contain cleansing agents to bind the oil in the skin at the sample point and reduce the effect thereof. Finally, a surfactant can also be included in the fluid composition. The surfactant improves the wetting of the tissue, creating a uniform interface. An antiseptic material can also be added to the index-matching medium.

In an alternative embodiment of the current invention, the index matching between the optical sensor elements and the tissue can be performed by a deformable solid. The deformable solid can alter its shape such that air gaps, due in part to the uneven surfaces of the skin, are minimized. Deformable solids can include at least gelatin, adhesive tape, and substances that are liquid upon application but become solid over time.

The index-matching medium preferably has a refractive index of between 1.30–1.45, more preferably between 1.35–1.40. Utilization of a refractive index in this range has been found to improve the repeatability and accuracy of the above method by improving optical throughput and decreasing spectroscopic variations unrelated to analyte concentration. Further, the index-matching medium should have a consistent refractive index throughout the composition. For example, no air bubbles should be present which cause changes in light direction.

In a preferred embodiment, the concentration of glucose in the tissue is determined by first measuring the light intensity received by the output sensor. These measured intensities in combination with a calibration model are utilized by a multivariate algorithm to predict the glucose concentration in the tissue. The calibration model empirically relates the known glucose concentrations in a set of calibration samples to the measured intensity variations obtained from said calibration samples. In a preferred embodiment, the multivariate algorithm used is the partial least squares method, although other multivariate techniques can be employed.

The use of an index-matching medium to couple the optical sensor's input element and output element to the skin surface reduces the likelihood that aberrant data will be acquired. The index-matching medium increases the repeatability and accuracy of the measuring procedure. Adverse effects on the input and output light energy by transmission through air or uneven surfaces of the skin having pockets of air are eliminated.

These and various other advantages and features of novelty which characterize the present invention are pointed out with particularity in the claims annexed hereto and forming a part hereof. However, for a better understanding of the invention, its advantages, and the object obtained by its use, reference should be made to the drawings which form a further part hereof, and to the accompanying descriptive matter in which there are illustrated and described preferred embodiments of the present invention.

BRIEF DESCRIPTION OF THE DRAWINGS

In the drawings, in which like reference numerals indicate corresponding parts or elements of preferred embodiments of the present invention throughout the several views.

DETAILED DESCRIPTION OF THE PREFERRED EMBODIMENTS

Figure 1:
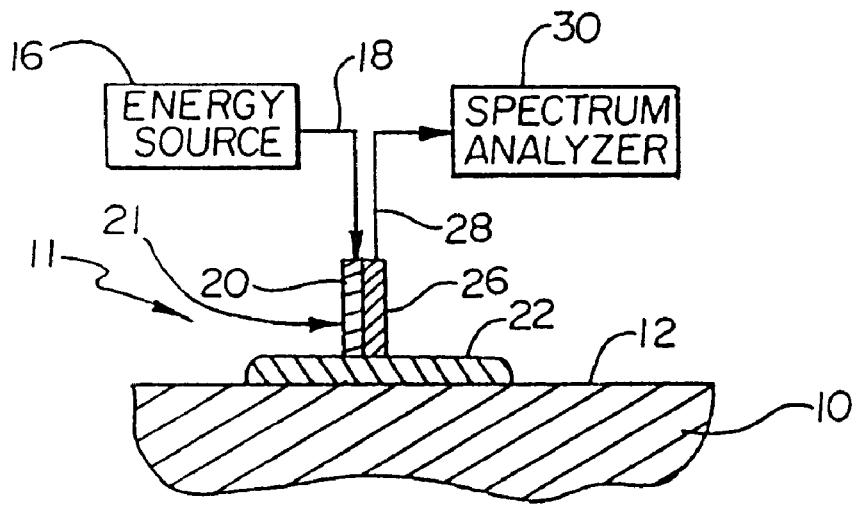
FIG. 1 is a partial cross-sectional view of a sensor element coupled to the skin surface via an indexing-matching fluid.

Detailed embodiments of the present invention are disclosed herein. However, it is to be understood that the disclosed embodiments are merely exemplary of the present invention which may be embodied in various systems. Therefore, specific details disclosed herein are not to be interpreted as limiting, but rather as a basis for the claims and as a representative basis for teaching one of skill in the art to variously practice the invention.

The present invention is directed to a method for non-invasive measurement of tissue constituents using spectroscopy. It has been found that the sample is a complex matrix of materials with differing refractive indices and absorption properties. Further, because the blood constituents of interest are present at very low concentrations, it has been found to be imperative to couple light into and out from the tissue in an efficient manner. The method of the present invention incorporates an index-matching medium, fluid or deformable solid, to improve the efficiency of coupling the light both into and out of the tissue sample.

Further, it has been found that means for equilibrating the concentration of glucose or other blood analyte between the vascular system and the tissue is critical to reduce or eliminate the lag time between blood capillary analyte or glucose concentration and interstitial tissue analyte or glucose concentration at the time of measurement. Thus, sample results of total tissue analysis are not skewed by the difference between blood glucose or other blood analyte concentration versus interstitial tissue glucose or other interstitial tissue analyte concentration as the method for non-invasive measurement of tissue constituents using spectroscopy is utilized.

Although described in detail with reference to non-invasive spectrographic analysis of blood analytes, the present invention, and particularly the means for equilibrating the concentration of analytes, may be used to measure analyte concentrations in virtually any tissue or fluid. Further, such measurements may be made non-invasively or by taking a sample of tissue or fluid after equilibration. For example, the present invention is suitable for use in conjunction with measuring glucose levels in interstitial fluid drawn from dermal tissue where measurement accuracy is greatly improved by first equilibrating the concentration of the analyte in blood with the concentration in the interstitial fluid which is sampled. Interstitial glucose levels are indicative of blood glucose levels and have been suggested as sufficient for diabetes management, as described by Bantle et al. in J. Lab. Clin. Med., 130:436–441, 1997, the disclosure of which is hereby incorporated by reference.

In addition, although described in detail with reference to glucose, the present invention is suitable for measuring virtually any analyte, whether in the blood, interstitial tissue, or other bodily media. For example, the present invention is suitable for measuring urea in blood, as described in co-pending U.S. patent application Ser. No. 09/182,340, filed Oct. 29, 1998, entitled "Apparatus and Method for Determination of the Adequacy of Dialysis by Non-Invasive Near-Infrared Spectroscopy", which is expressly incorporated herein by reference. Primarily for purposes of illustration, not limitation, the present invention is described with particular reference to blood glucose measurements.

The means for equilibrating the concentration of glucose or other analyte concentration between the first fluid compartment or blood and second fluid compartment or tissue preferably causes an increase in both the volume of blood and the rate of blood flow in the dermis and subcutaneous tissue local to the point of analysis in order to increase the rate of equilibration of the surrounding interstitial fluid. In this way, the delivery of glucose to the interstitial fluid and tissue as a whole is increased sufficiently so that during a single sitting, equilibrium is reached prior to measuring absolute analyte concentration. In terms of the dye and glass of water analogy, the drip rate of the dye into the glass container would increase significantly (say from two drops per minute to 20 drops per minute). The result is clearly an increase in the rate of equilibrium between the blood or vascular compartment and the interstitial compartment. Most importantly, the interstitial water compartment and the tissue glucose as a whole will be in or near equilibrium with the blood glucose concentration. Utilizing the means for equilibration and waiting until equilibration is confirmed dramatically improves the accuracy of tissue measurements as a predictor of actual or absolute blood glucose.

Physiological increases in the rate of blood flow and the volume of blood in the skin are chiefly the result of dilatation of pre-capillary sphincters. There are a number of methods for inducing such changes within the scope of the present invention which are mediated by efferent nerves supplying the arteriolar precapillary sphincters or by the effects of soluble vasodilators either intravascular or interstitial. Heating, either locally on the skin or centrally (for instance, the febrile state or during exercise) is a strong inducer of skin blood flow as anyone who has taken a hot shower can attest. Topical pharmacologic agents applied to the skin such as nicotinic acid result in marked increases in superficial blood flow and volume. Other topical agents can include methyl nicotinamide, minoxidil, nitroglycerin, histamine, menthol, capsaicin and mixtures thereof. Subcutaneous or intravascular injections of vasoactive substances such as methyldopa also cause precapillary sphincter relaxation with a commensurate decrease in flow resistance and increase of blood flow.

Local skin heating at the site of the analyte measurement is preferred resulting in significant increases in the dermal and subcutaneous blood flow. Skin flow measurements made during stepped heating of a 6 cm area revealed flow increases of 1000%. There was also transition in the forearm from undetectable flow, that is pulseless or waveless flow, to systolic-diastolic waves representing arteriolar pulsatile flow when pre-capillary sphincters are opened wide. The local temperature threshold for pulsatile flow is slightly higher than core temperature or 38° C. Thus, the local stimulus for dissipation of heat is when the net heat flux is inward or when the external temperature is greater than the body temperature. Fortunately, the threshold is much lower than the temperature needed to thermally damage skin. As noted above, heating can be applied locally or centrally, but it can also be applied to other areas of the body to induce increased blood flow elsewhere. For instance, the contralateral or opposite arm can be heated (usually the entire arm) to induce an increase in the arm under scrutiny.

The other methodology that does not involve damage to the tissue is the application of topical pharmacologic agents that diffuse into the dermis and subcutaneous tissue and directly cause local vasodilation, as stated above. Although they are easy to use and can result in sustained increases in local dermal blood flow equivalent to that induced by heating, they do require application of a foreign substance to the area to be analyzed. Additionally, these agents must diffuse into the skin in order to exert their pharmacologic effect.

Increasing dermal blood flow in order to hasten dermal equilibration of glucose concentration in the blood vessels and interstitial fluid is most easily accomplished by locally heating or application of a rubrifractant to the area under measurement. Local heating is accomplished by placing the tissue in contact with a controlled heat source. The heat source must have enough thermal mass to maintain the local tissue above the threshold temperature. A simple temperature feed back system can assure the maintenance of stable temperature despite loss to the environment and tissue as well as protect against overheating and thermal tissue damage.

In preferred near-infrared measurement devices of the present invention, infrared energy is coupled into the skin via optical lenses, thus it is preferred to heat and maintain the lens at a desired temperature. The lens itself heats the local tissue in order to increase the blood flow and decrease the measurement errors due to lag of the tissue with respect to the blood. The lens mount can contain the heating elements and temperature sensor that maintain the lens and local arm at the desired temperature. The incident light beam and the reflected infrared energy beams are passed through the same heated lens.

Generally, enhanced equilibration begins as soon as increased blood flow is established at the measurement site. The amount of equilibration required for an accurate reading is a function of amount of concentration mismatch present between the vascular fluid compartment and the tissue fluid compartments, the rate of equilibration and the desired accuracy of the tissue measurement when compared to blood glucose measurement. The more equilibration allowed to occur, of course, the more accurate the agreement between the non-invasive tissue measurement and blood glucose measurement. For general clinical applications, the desired level of equilibration should be less than 80%.

If heat is utilized to cause the increase in blood flow, the time to reach the desired level of equilibration depends on the temperature of the heat source, the temperature of the tissue, the heat conductivity of the heat applicator, the heat conductivity of the tissue, the heat conductivity of the interface between the heat source and the tissue, and the amount of dis-equilibrium between tissue and blood. Generally, the time to reach the desired level of equilibration is inversely proportional to the temperature difference between the heat source and the tissue, and directly proportional to the conductivity of the heat applicator, interface and tissue. Alternatively, if a rubrifractant is utilized to cause the increase in blood flow, the time to reach the desired level of equilibration depends on the vasodilating characteristics of the particular rubrifractant selected. Of course, the time to reach equilibration also depends on the particular tissue characteristics and physiological characteristics of the test subject, which vary from person to person. Acknowledging that characteristics specific to a particular test subject cannot be readily controlled, average characteristics may be assumed.

The average core body temperature of a human is 38° C. and the average skin temperature of a human is 35° C. Thus, if heat is utilized to increase blood flow, enhanced equilibration begins as soon as the skin temperature rises above 35° C. Preferably, the skin temperature is allowed to rise about 5° C., and more preferably about 7° C. for sufficient increase in the rate of equilibration. Assuming a heat source temperature of about 40° C. to 42° C., equilibration begins almost immediately upon contact (i.e., heat transfer) with the tissue, and full temperature stabilization of tissue water occurs at about 3 to 4 minutes thereafter. In preferred methods, three minutes of time is required to establish sufficient temperature stability of tissue water with a heat source at 40° C., although in some subjects less time is required. Overall, three minutes generally ensures that temperature stability has been reached and a state of increased equilibration established in all patients. Due to the many items listed previously, equilibration between the vascular and tissue fluid compartments can occur over varying time periods and multiple readings may be taken to confirm equilibrium and monitor the direction and rate of change of analyte concentration as detailed below.

In summary, it has been found that using a means for equilibrating the glucose or analyte concentration between the vascular system and the tissue greatly facilitates the accuracy of non-invasive infrared analysis of blood analytes when compared to standard blood measurement. In preferred methods, the interstitial/dermal water temperature is increased, which can be achieved by local heating of the skin surface for a period of time. However, more than heating of the skin surface is required to achieve increased accuracy. When the arm is placed in contact with a heated surface, the external surface of the skin, the epidermis, rapidly equilibrates with the heated surface. The transfer of heat into the deeper tissue areas, however, takes a finite period of time. Thus, there is an additional delay before the interstitial water becomes sufficiently or fully equilibrated. The increase in tissue temperature results in increased blood flow to the heated area. Thus, the result of increased tissue temperature and the corresponding increase in blood flow results in a condition that increases the exchange of glucose between the vascular and interstitial compartments. The increased exchange rate results in increase agreement between the blood capillary reference value for the analyte of interest and the noninvasive optical measurement. It is only when sufficient time is allowed to reach near equilibration that increased accuracy is achieved.

To determine the delay between placement of the arm in contact with a heated surface during optical sampling and increased temperature of the tissue water, an experiment was conducted. An unheated arm was placed in contact with a tissue sampling device controlled to a temperature of 40° C. A near infrared model for predicting tissue water temperature was applied to the resulting spectra. The study was repeated on three subjects. The results of the spectroscopic analysis for the prediction of tissue water temperature showed the tissue water reached greater than 90% equilibration with the temperature of the heating plate in less than 4 minutes. It was noted that there is time to equilibration differences between the patients tested. The tissue water temperature began to increase upon contact with the heated arm plate. It was also noted that the near infrared light penetrating the tissue also contributes to heating of tissue water due to absorption.

The preceding experiment examined tissue spectra from the perspective of increased tissue water temperature. The influence of tissue heating can also be examined by looking at increased blood flow and blood volume. If tissue water temperature increases above core body temperature, vasodilatation will occur as the body attempts to keep the tissue in temperature equilibrium. Changes in blood flow and blood volume can be assessed through the use of a laser Doppler. A study with 5 patients was conducted where the arm was placed in contact with a sampling device heated to 42° C. The sampling device contained a MedPacific LD6000 laser Doppler. All 5 patients demonstrated both increased blood flow and blood volume by 3 minutes. Thus, heating of the tissue results in a condition that increases the exchange of glucose and other analytes between the vascular space and the interstitial space, which upon waiting a sufficient time, results in equilibration of analytes between compartments.

The present invention utilizes light energy in the near-infrared region of the optical spectrum as an energy source for analysis. Water is by far the largest contributor to absorption in tissue in the near-infrared region because of its concentration, as well as its strong absorption coefficient. It has been found that the total absorption spectrum of tissue, therefore, closely resembles the water spectrum. Less than 0.1 percent of the absorption of light is from, for instance, a constituent such as glucose. It has been further found that tissue greatly scatters light because there are many refractive index discontinuities in a typical tissue sample. Water is perfused through the tissue, with a refractive index of 1.33. Cell walls and other features of tissue have refractive indices closer to 1.5 to 1.6. These refractive index discontinuities give rise to scatter. Although these refractive index discontinuities are frequent, they are also typically small in magnitude and the scatter generally has a strong directionality towards the forward direction.

This forward scatter has been described in terms of anisotropy, which is defined as the cosine of the average scatter angle. Thus, for complete backwards scatter, meaning that all scatter events would cause a photon to divert its direction of travel by 180 degrees, the anisotropy factor is −1. Likewise, for complete forward scatter, the anisotropy factor is +1. In the near infrared, tissue has been found to have an anisotropy factor of around 0.9 to 0.95, which is very forward scattering. For instance, an anisotropy factor of 0.9 means that an average photon of light only scatters through an angle of up to 25 degrees as it passes through the sample.

In analyzing for an analyte in tissue, measurements can be made in at least two different modes. It is recognized that one can measure light transmitted through a section of tissue, or one may measure light reflected or remitted from tissue. It has been recognized that transmission is the preferred method of analysis in spectroscopy because of the forward scattering of light as it passes through the tissue. However, it is difficult to find a part of the body which is optically thin enough to pass near infrared light through, especially at the longer wave lengths. Thus, the preferred method for measurement in the present invention is to focus on the reflectance of light from the sample.

Photons reflect and refract at refractive index discontinuities, and so light impinging on tissue immediately has a small reflectance at the tissue surface. This is referred to as specular reflectance. Since this light does not penetrate into the tissue, it contains little information about the tissue constituents. This is especially true in light of the physiology of skin, which possess an outward layer which is essentially dead and lacks concentration values of the analytes generally considered of interest in a sample. Thus, reflected light energy containing analyte information is that light which is reflected back to the surface through refractive index discontinuities deeper within the tissue sample. This reflected light energy is referred to as diffusely reflected light.

Applicants have found that a large fraction of incident photons are absorbed in the tissue. Those photons which are available for coupling back out of the tissue are likely diverted in their angular path. In fact, by definition, a photon must change direction in order to exit the tissue in a direction towards the input optic. Applicants, however, have found that a large problem associated with detection is associated with the refractive index discontinuity between the average tissue refractive index and the refractive index of air outside of the tissue. It has been found that this discontinuity acting on incident light leads to a refraction and a small specular reflectance of less than about 5 percent. However, on the way out, the discontinuity gives rise to a critical angle phenomenon. Because the photon is traveling from a high refractive index medium to a lower one, a critical angle exists above which a photon is totally internally reflected and will not escape the tissue sample. This critical angle for photons traveling from tissue to air has been found to be about 46 degrees, which presents a problem. A photon normally incident on the tissue surface must deviate through a large angle to exit. Because of the forward directionality of scattering, this is difficult for a photon to do, and it is very likely to make a grazing or high angle incidence with the tissue and air interface. The grazing incidence photons will not escape because the critical angle is exceeded.

Applicants have found a solution for the differences in refractive index associated with coupling light energy exiting tissue to an analytical instrument. The solution is the use of an immersion fluid which has very low absorptivity in the spectral range of interest, and has a viscosity compatible with good flow and coverage, while having a refractive index which closely matches tissue. In preferred embodiments, the index matching fluid is preferably minimally or essentially non-absorbing of light energy in the wavelengths relevant to the blood analyte under study. The fluid is thus non-spectroscopically active at desired wavelengths. However, it is believed a minimally absorbing index-matching fluid, for example one that absorbs less than about 10% of the light energy of analyte relevant wavelengths, could still be utilized. A preferred material is a fluorinated, chlorinated hydrocarbon polymer oil manufactured by Occidental Chemical under the tradename FLUOROLUBE. FS5 is a preferred FLUOROLUBE. These oils have a refractive index of about 1.38, are non-toxic, and Applicants have found that it has a spectral signature in the near infrared region which is minimal.

Figure 2:
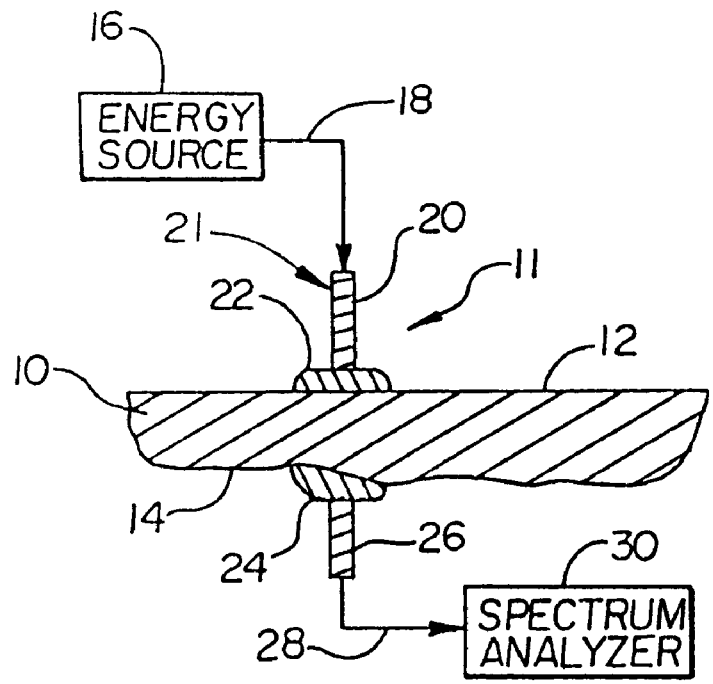
FIG. 2 is a partial cross-sectional view of an alternative embodiment of a sensor element coupled to opposite sides of a skin surface via an indexing-matching fluid.

Now referring to FIGS. 1 and 2, partial cross-sectional views of two preferred embodiments of an apparatus for non-invasively measuring a blood analyte concentration are depicted. The depictions in FIGS. 1 and 2 are schematic to depict the concept of utilizing an index-matching medium 22 in conjunction with a non-invasive sensor element 11 operatively connected to an energy source 16 and a spectrum analyzer 30. The relative size, shape and detail of physical components are not depicted.

The apparatus depicted in FIG. 1 and the apparatus depicted in FIG. 2 generally include three elements, an energy source 16, a sensor element 11, and a spectrum analyzer 30. The embodiment of FIG. 1 depicts the sensor element as including an input element 20 and an output element 26, which can include a single lens system for both input and output light energy. The input element 20 and output element 26 are in contact with a common skin surface 12 of an analyte-containing tissue 10. The alternative embodiment of FIG. 2 depicts an alternative sensor element 11 arrangement, wherein the input element 20 and output element 26 are arranged on opposing surfaces 12, 14 of an analyte containing tissue 10. Both embodiments function to give a measure of the absorption of infrared energy by the analyte-containing tissue 10. However, the embodiment of FIG. 1 is utilized to measure the quantity of light energy which is reflected from the analyte-containing tissue 10 by the analyte components therein. In contrast, the embodiment of FIG. 2 measures the transmission of light energy through the analyte-containing tissue 10. In either embodiment, the absorption at various wavelengths can be determined by comparison to the intensity of the light energy from the energy source 16.

The energy source 16 is preferably a wide band, infrared black body source. The optical wavelengths emitted from the energy source 16 are preferably between 1.0 and 2.5 $\mu$m. The energy source 16 is operatively coupled to a first means for transmitting infrared energy 18 from the energy source to the input element 20. In preferred embodiments, this first means 18 is simply the transmission of light energy to the input element 20 through air by placing the energy source 16 proximate the input element 20.

The input element 20 of the sensor element 11 is preferably an optical lens which focuses the light energy to a high energy density spot. However, it is understood that other beam focusing means may be utilized in conjunction with the optical lens to alter the area of illumination. For example, a multiple lens system, tapered fibers, or other conventional optical beam-shaping devices could be utilized to alter the input light energy.

In both embodiments depicted in FIGS. 1 and 2, an output sensor 26 is utilized to receive reflected or transmitted light energy from the analyte containing tissue 10. As described in conjunction with a method of analysis below, the embodiment of FIG. 1 has an output sensor 26 which receives reflected light energy, while the embodiment of FIG. 2 includes an output sensor 26 which receives transmitted light through the analyte-containing tissue 10. As with the input element 20, the output element 26 is preferably an optical lens. Other optical collection means may be incorporated into an output element 26, such as a multiple lens system, tapered fiber, or other beam-collection means to assist in directing the light energy to the spectrum analyzer 30.

A second means for transmitting infrared energy 28 is operatively connected to the output element 26. The light transmitted through the second means for transmitting infrared energy 28 is transmitted to the spectrum analyzer 30. In a preferred embodiment, the operative connection to the output element includes transmission of the reflected or transmitted light energy exiting the output element through air to the spectrum analyzer 30. A mirror or series of mirrors may be utilized to direct this light energy to the spectrum analyzer. In a preferred embodiment, a specular control device is incorporated to separate the specular reflected light from diffusely reflected light. This device is disclosed in co-pending and commonly assigned application Ser. No. 08/513,094, filed Aug. 9, 1995, and entitled "Improved Diffuse Reflectance Monitoring Apparatus", now U.S. Pat. No. 5,636,633, issued Jun. 10, 1997, the disclosure of which is incorporated herein by reference.

The means for equilibrating the concentration of glucose or another analyte between fluid compartments is depicted in FIGS. 1 and 2 as heat source 21. It is recognized, as previously disclosed, that means for equilibrating can be incorporated in the index-matching medium 22.

In practicing the method of the present invention, an analyte-containing tissue 10 area is selected as the point of analysis. This area can include the skin surface 12 on the finger, earlobe, forearm, or any other skin surface. Preferably, the area for sampling includes blood vessels near the surface, and a relatively smooth, uncalloused surface. A preferred sample location is the underside of the forearm.

A quantity of an index-matching medium 22, whether fluid or deformable solid, is then placed on the skin surface 12 in the area to be analyzed. The sensor element 11, which includes the input element 20 and the output element 26, as depicted in the embodiment of FIG. 1, is then placed in contact with the index-matching medium 22. Alternatively, a quantity of index-matching medium 22 can be placed on the sensor element 11, which is then placed in contact with the skin surface 12 with the index-matching medium 22 disposed therebetween. In either procedure, the input element 20 and output element 26 are coupled to the analyte-containing tissue 10 or skin surface 12 via the index-matching medium 22. The coupling of the sensor element 11 with the skin surface via the index-matching medium 22 eliminates the need for light energy to propagate through air or pockets of air due to a space between the probe and the skin surface 12 or irregularities in the skin surface 12.

Means for equilibrating the concentration of glucose or other analyte between the vascular system and tissue in the area of analysis are utilized to equilibrate such concentration. For example, the sensor element may be heated to between 38° C. and 42° C. and placed in contact with the tissue area for about 2 to 5 minutes prior to analyzing the tissue for analyte concentration. This has been found to be sufficient time to not only heat the tissue, but more importantly, allow for sufficient analyte equilibration between fluid compartments having the analyte therein.

In analyzing for the concentration of glucose in the analyte-containing tissue 10, light energy from the energy source 16 is transmitted through the first means for transmitting infrared energy 18 into the input element 20. The light energy is transmitted from the input element 20 through the index-matching medium 22, to the skin surface 12. The light energy contacting the skin surface 12 is differentially absorbed by the various components and analytes contained below the skin surface 12 with the body (i.e., blood within vessels) therein. In a preferred embodiment, the non-absorbed light energy is reflected back to the output element 26 upon propagating again through the index-matching medium 22. The non-absorbed light energy is transmitted via the second means for transmitting infrared energy 28 to the spectrum analyzer 30.

In the alternative embodiment of FIG. 2, the input element 20 is placed in contact with a first quantity of index-matching medium 22 on a first skin surface 12, while the output element 26 is placed in contact with a second quantity of index-matching medium 24 on an opposing skin surface 14. As with the previous embodiment, the index-matching medium 22 can be first placed on the input element 20 and output element 26 prior to contact with the skin surface 12. With this alternative embodiment, the light energy propagated through the input element 20 and first quantity of index-matching medium 22 is differentially absorbed by the analyte-containing tissue 10, while a quantity of the light energy at various wavelengths is transmitted through the analyte-containing tissue 10 to the opposing or second skin surface 14. From the second skin surface 14, the non-absorbed light energy is propagated through the second quantity of index-matching medium 24 to the output element 26 with subsequent propagation to the spectrum analyzer 30 for calculation of the analyte concentration.

As previously stated, the index-matching medium 22 of the present invention is a key to the improved accuracy and repeatability of the method described above. The index-matching medium can preferably be a fluid composition containing chlorofluorocarbons. The composition can also be a mixture of chlorofluorocarbons and perfluorocarbons. A preferred composition includes chlorotrifluoroethylene. A preferred composition contains about 80% to about 99.8% by weight of chlorofluorocarbons. As previously stated, the present invention utilizes an index-matching fluid to optimize the input and output of light energy to and from a sample containing an analyte of interest to be measured. In its broadest sense, the index-matching fluid of the present invention can be any fluid which creates an improved optical interface over that interface which results from simply placing the probe of the present invention on a skin surface. Absent the index-matching fluid of the present invention, this interface can include gaps which are air filled and cause detrimental refraction of light both going into the tissue and exiting the tissue. Thus, any index-matching fluid having a refractive index closer to that of the tissue at about 1.38 versus the refractive index of air of about 1.0 would provide an improved interface.

Applicants have also recognized that the usefulness of the apparatus of the present invention requires that the coupling of the sensor be repeatable and that the results be an accurate reflection of the blood glucose level of the patient. To this end, Applicants have found that it is preferable for the index-matching fluids of the present invention to contain diagnostic additives and/or physiological additives. The diagnostic additives provide an assessment of the quality of the lens to tissue interface and/or an assessment of the instrument's present performance, while the physiological additives alter the physiology of the tissue to correct for differences in tissue analyte concentration versus blood analyte concentration. A discussion of these additives follows.

The non-invasive measurement of glucose in tissue by the present invention is improved by placing an additive into the index-matching fluid that allows evaluation of the thickness of the fluid when the tissue is placed in contact with the instrument. In preferred embodiments, the additive also provides a calibration of the instrument by including a compound of known high absorption at a specified wavelength of light. Such additives also further assure that the correct index-matching fluid is being utilized for the instrument.

Since an index-matching fluid inherently causes a change of height in the tissue above the sample probe, the measurement of this height can aid in the overall glucose or other analyte measurement, while allowing a path length correction to be applied to the spectral measurement as a function of the tissue height above the sampler. This can insure a reproducible, consistent height is achieved before commencing the spectral measurement of the tissue, and further allows for the adjustment of the height before commencing the spectral measurement of the tissue. In this way, the user can be certain that spurious results are not achieved due to excess matching fluid height, insufficient index-matching fluid being utilized, or some other misplacement of the tissue surface relative to the analyzer.

Laboratory spectrometers utilize a Fourier Transform system which incorporates a laser reference signal to establish the wavelengths and guarantees that the instrument is calibrated. However, it is likely instruments that are affordable for an end user will not use a laser, but rather will be dispersion type instruments such as gratings, CCD arrays and others. With such instruments, it is important to make certain that calibration is proper prior to each analysis of blood analyte. To this end, Applicants have found that the addition of an additive which includes a well-defined spectral feature at a known wavelength of light can be utilized to assure calibration.

The use of a known spectrally active additive to the index-matching fluid also insures that the end user is using a correct index-matching fluid for which the instrument has been calibrated and programmed. The use of a different index-matching fluid could result in an error in the non-invasive analyte measurement by absorbing light energy in the areas of interest for the particular analyte.

To accomplish the above repeatability, accuracy and quality assurance, a spectroscopically active agent is preferably added to the index-matching fluid. The agent preferably has sharp bands of absorption outside the region of interest to measure the blood analyte. For example, in a preferred method for glucose analysis, the agent would be active outside the ranges of 4200–4900 and 5400–7200 wave numbers. The agent could also be active within this range so long as there is no significant overlap with wavelengths actually used to calculate glucose concentration. The additive can be manufactured by placing an appropriate functional group on perfluorinated hydrocarbons. The perfluorinated hydrocarbons are spectrally inactive in the region of interest, however, the functional group placed upon the perfluorinated hydrocarbons may be spectrally active. Further, these functional groups do not interfere with the analysis of the blood analyte of interest. Exemplary compounds include perfluoro-2-butyltetrahydrofuran and perfluorosuccinyl chloride.

In an alternative embodiment, the index-matching fluid and diagnostic additive can comprise the same fluid which provides both functions. For example, perfluoro-2-butyltetrahydrofuran can be utilized as an index-matching medium which improves the optical interface, and at the same time includes a functional group which makes the compound spectrographically active in a desired range for diagnostic purposes.

As previously stated, the near infrared light energy of the present invention is preferably utilized to measure a blood analyte such as glucose. It is also stated that the light energy interrogates the skin as a whole, while the blood vessels make up less than 10% of the skin volume. Therefore, in reality the total skin glucose content is being used as a surrogate for blood glucose concentration. This fact can lead to inaccurate test results if there is a large difference between the tissue glucose concentration and the blood vessel glucose concentration, such as in times of rapidly rising or falling blood glucose levels. Blood glucose can rise acutely after a meal or during glucose production by the liver, while there is a commensurate but lagged rise of the skin glucose concentration. This lag, due to the finite time required for the glucose to diffuse into the greater skin water compartment, can take minutes to tens of minutes depending upon the magnitude of the rise and the surface area of the capillaries available for diffusion. Applicants, therefore, equilibrate the analyte concentration between fluid compartments prior to relying on the accuracy of the total skin glucose content as a surrogate for blood glucose concentration. Applicants have also discovered the usefulness of taking multiple samples prior to and during equilibration procedure. As detailed below, such readings can be utilized to predict the direction and rate of charge of glucose or other analyte in the blood so that the therapeutic response can be optimized.

During actual use of a non-invasive apparatus of the present invention, Applicants have found that the surface of a patient's arm or sample area on such arm will be approximately at room temperature. At room temperature, there exists a concentration difference between the tissue and the blood if the patient's glucose concentration is in disequilibrium, such as during times of changing glucose based on activity or food ingestion.

For clarity, the room temperature arm will be called a "cold arm". If the cold arm is placed in the optical sampling device of the present invention and heated in accordance with Applicants' disclosed method of equilibration, the concentration difference between the blood and tissue will decrease over time due to the improved exchange between these two fluid compartments. In simple terms, a cold arm glucose measurement by the infrared non-invasive method and apparatus of the present invention will generate a glucose or other analyte measurement that is representative of past glucose or analyte levels. As the arm warms up and the blood and tissue glucose or other analyte levels are allowed to equilibrate, the non-invasive measurement will represent current glucose levels. Due to the fact that the cold arm represents a past glucose level, both the direction and rate of change of blood glucose or other analyte can be determined. Thus, Applicants have found that within a single non-invasive measurement sitting, which involves multiple readings, much information can be gathered in a short period of time by utilizing Applicants' method of equilibrating analyte concentrations in fluid compartments. This information includes the direction of glucose or other analyte change, the rate of change over the preceding period, and the absolute glucose concentration in the blood upon reaching equilibrium.

In a preferred method, the patient would place their cold arm in the non-invasive measurement device. The monitor would then make a non-invasive measurement during the insertion period. If the patient is at a stable glucose or other analyte of interest concentration and no equilibration between the tissue and blood was necessary, the non-invasive glucose reading would be relatively constant during the equilibration period. For example, the readings over the first three minutes would be approximately the same. However, if the patient's glucose or other analyte was changing rapidly, or had been changing rapidly before the insertion, the non-invasive measurements would change rapidly over time due to the equilibration between the tissue and the blood during the equilibration period. During a period of increasing blood glucose concentration, the test measurement on the cold arm would generate a reading that would be actually below the blood value. As the arm equilibrates, such as by heating, the blood and tissue glucose values rapidly equilibrate. Multiple non-invasive tissue measurements can be made during a single sitting to monitor both the absolute change in magnitude and the rate of change in magnitude of the total tissue analyte measurement. Because the total tissue measurement increases during the equilibration period, it is clearly indicated that the blood concentration of the analyte measured is increasing as there has not been time for the tissue concentration to catch up based on the natural lag between fluid compartments.

In contrast to a period of increasing blood analyte concentration or glucose concentration, a period of decreasing concentration would be indicated by a higher glucose concentration in the tissue than that in the blood. Thus, the non-invasive prediction of the cold arm would be above the actual blood concentration. This disequilibrium would be indicated upon activation of the means for equilibrating concentrations within fluid compartments and commensurate rapid decrease in the total tissue analyte concentration as equilibrium is achieved.

In summary, the arm, in its native state, will exhibit disequilibrium between tissue and blood glucose concentrations when the glucose concentration is changing. A non-invasive measurement under conditions of disequilibrium will provide information about past blood glucose concentrations. As the condition of disequilibrium is resolved, the non-invasive measurement becomes a measurement of current blood glucose concentration. The condition of blood/tissue disequilibrium can be resolved through multiple methods. As mentioned above, heat resolves the disequilibrium condition. Further, other methods resolve disequilibrium conditions as previously disclosed. Due to the fact that in the present embodiment, measurements are made under a condition of disequilibrium, if a patient's glucose has been changing, the non-invasive device can provide information regarding both the direction and rate of change of the patient's glucose or other analyte concentration so that an accurate prediction of treatment may be made in response to the information.

In an alternative embodiment of the present invention, the compound used as an index-matching fluid can contain a hydrophilic additive, such as isopropyl alcohol. The hydrophilic additive is believed to tie up the moisture in the skin surface to improve the interface between the medium and the skin. Further, the index-matching medium can contain cleansing agents to bind the oil in the skin at the sample point and reduce the effect thereof. A surfactant can also be included in the composition. The surfactant improves the wetting of the tissue, thus improving contact. Finally, an antiseptic compound can be added to the index-matching medium.

In an alternative embodiment of the current invention, the index matching between the optical sensor elements and the tissue can be performed by a deformable solid. The deformable solid can alter its shape such that air gaps, due in part to the uneven surfaces of the skin, are minimized. Deformable solids can include at least gelatin, adhesive tape, and substances that are liquid upon application but become solid over time.

The index-matching medium, preferably has a refractive index of 1.30–1.45, more preferably from 1.35–1.40. Utilization of a refractive index in this range has been found to improve the repeatability and accuracy of the above method. It is recognized that the refractive index of the index-matching medium must be consistent throughout the composition to prevent refraction of light energy as it passes through the medium. For example, there should be no air bubbles present in the index-matching medium which could cause a discontinuity in refractive index.

In a preferred embodiment, the concentration of glucose in the tissue is determined by first measuring the light intensity received by the output sensor. These measured intensities in combination with a calibration model are utilized by a multivariate algorithm to predict the glucose concentration in the tissue. The calibration model empirically relates the known glucose concentrations in the calibration samples to the measured intensity variations obtained from said calibration samples. In a preferred embodiment, the multivariate algorithm used is the partial least squares method, although other multivariate techniques can be employed.

The input infrared energy from the input element sensor is coupled to the analyte-containing sample or blood through the index-matching medium 22. There is, thus, differing absorption at several wavelengths of the infrared energy as a function of the composition of the sample. The differing absorption causes intensity variations of the infrared energy passing through the analyte containing samples. The derived intensity variations of the infrared energy are received by reflectance or transmittance through the analyte-containing sample by the output element of the sensor, which is also coupled to the blood or analyte-containing sample through the index-matching medium 22.

The spectrum analyzer 30 of the present invention preferably includes a frequency dispersion device and photodiode array detectors in conjunction with a computer to compare the data received from such devices to the model discussed above. Although preferable, other methods of analyzing the output energy may be utilized.

The frequency dispersion device and photodiode array detectors are arranged so that the array includes multiple output leads, one of which is assigned to a particular wavelength or narrow range of wavelengths of the energy source 16. The amplitude of the voltage developed on each of the leads is commensurate with the intensity of the infrared energy incident on each particular detector in the array for the wavelength of the source associated with that detector. Typically, the photodiodes of the array detector are passive, rather than photovoltaic, although photovoltaic devices may be employed. The diodes of the array detector must be supplied with DC power supply voltage as derived from a power supply and coupled to the diodes of the array detector via a cable. The impedance of the diode elements of the array detector are changed as a function of the intensity of the optical energy incident thereon in the pass band of the energy source 16 associated with each particular photodiode element. The impedance changes can control the amplitude of the signal supplied by the array detector to a random access memory computer.

The computer includes a memory having stored therein a multivariate calibration model empirically relating the known glucose concentration in a set of calibration samples to the measure intensity variations from said calibration samples, at several wavelengths. Such a model is constructed using techniques known by statisticians.

The computer predicts the analyte concentration of the analyte-containing sample 10 by utilizing the measured intensity variations, calibration model and a multivariate algorithm. Preferably, the computation is made by the partial least squares technique as disclosed by Robinson et al. in U.S. Pat. No. 4,975,581, incorporated herein by reference.

It is has been found that considerable improvement in detection precision is obtained by simultaneously utilizing at least several wavelengths from the entire spectral frequency range of the energy source 16 to derive data for a multivariate analysis. The multivariate method allows both detection and compensation for interferences, the detection of meaningless results, as well as for modeling many types of non-linearities. Since the calibration samples used to derive the models have been analyzed on a multivariate basis, the presence of unknown biological materials in the analyte containing tissue 10 does not prevent or distort the analysis. This is because these unknown biological materials are present in the calibration samples used to form the model.

The partial least squares algorithm, calibration model and measured intensity variations are employed by the computer to determine the concentration of the analyte in the analyte containing tissue 10. The indication derived by the computer is coupled to conventional alphanumeric visual displays.

Experimental

Example 1

Figure 3:
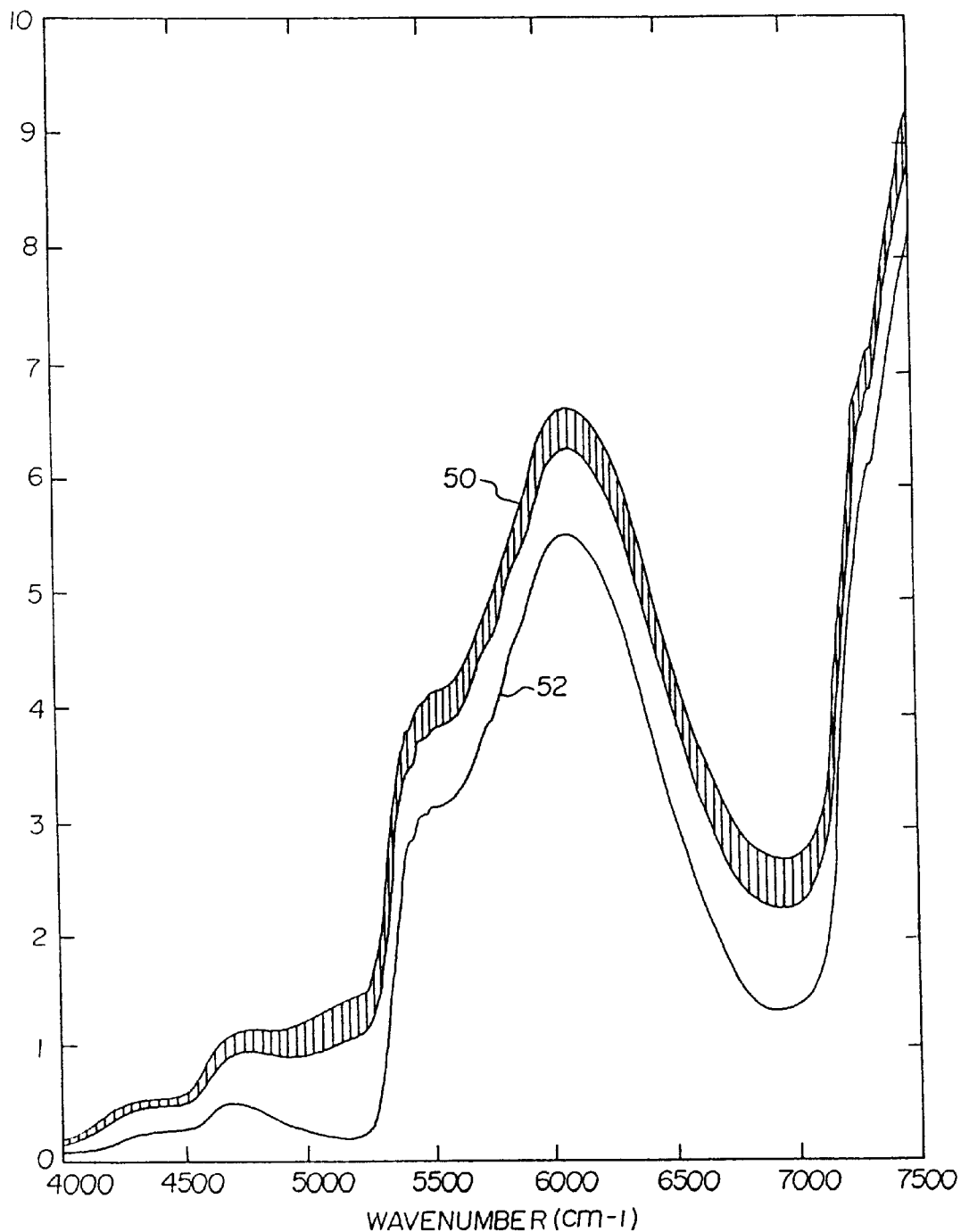
FIG. 3 is a graphical representation of experimental data showing the improvement in accuracy and repeatability of a sensor coupled to the skin via an index-matching medium.

Comparative testing was conducted to document the effect of utilizing an index-matching medium versus no index-matching medium on the same apparatus. Reference should be made to FIG. 3 which is a graphical representation of the results of the experiment, wherein line 50 represents analysis without the index-matching medium, and line 52 documents the improved accuracy of the result when the sensor element is coupled to the skin surface via an index-matching medium. To conduct the test, forearm sampling was conducted with and without the index-matching medium with a two minute time resolved data collection.

The apparatus utilized to conduct the experiment included a Perkin-Elmer (Norwalk, CT) System 2000 Fourier Transform Infrared Spectrometer (FTIR) with a 4 mm DIA indium antimonide (InSb) single element detector. The light source was a 100 watt quartz tungsten halogen light bulb from Gilway Technical Lamp (Woburn, Mass.). The interferometer employed an infrared transmitting quartz beamsplitter. Data collection was via a transputer link to a PC running Perkin-Elmer TR-IR software. Data visualization was accomplished in Matlab (MathWorks, Natick, Mass.). Sampling optics were constructed in-house and consisted, in part, of the optical system described in co-pending application Ser. No. 08/513,094, filed Aug. 9, 1995, entitled "Improved Diffuse Reflectance Monitoring Apparatus", now U.S. Pat. No. 5,636,633, issued Jun. 10, 1997. All instrument parameters were identical for the collection of both spectra.

The experimental procedure was as follows. The sampling surface consisted of a $MgF_2$ hemisphere mounted with its radiused side facing downward, and its flat surface placed horizontally. Light was launched into the hemisphere from below. The flat surface of the hemisphere, the mount for the hemisphere, and the holder for the mount all comprised a flush, horizontal sampling surface. The patient's arm was placed down on this surface, such that the underside of the forearm rested against the hemisphere sampling surface. The forearm area had previously been shaved and washed with soap and water, then swabbed with isopropyl alcohol. The arm was then covered with a blood pressure cuff which was inflated to a pressure of 30 mm Hg. The cuff acted to hold the arm in place and to prevent motion of the arm relative to the hemisphere. The sampling surface was held at a constant temperature of 28° C. by resistance heater elements and a thermocouple feedback device. After the arm was situated in the device, it was allowed to equilibrate for 30 seconds prior to sampling.

Referring to FIG. 3, the top trace, labeled 50, shows the result obtained when sampling in the previously described mode in the absence of index-matching medium. In the bottom trace, labeled 52, 100 microliters of chlorotrifluoroethene was applied to the surface of the hemisphere prior to placing the arm. There are several notable differences. Most apparent is the spread of the data. 50 and 52 are each comprised of multiple spectra. With FLUOROLUBE, all of the spectra overlay each other quite closely. This indicates that the interface is quite stable. Without FLUOROLUBE, the interface is extremely unstable. Also, notable is the data near 5200 $cm^{-1}$. This is the position of the strongest water band. Without FLUOROLUBE, this band appears weaker, since it is contaminated with specular light. In fact, note that the spread of the data is largest under this band. In fact, the difference between the two traces can be attributed largely to spurious energy from specular contamination.

Example 2

Tests were conducted to demonstrate the effect of utilizing means for equilibrating the concentration of glucose between the vascular system and tissue. The results are depicted graphically in FIGS. 4 and 5.

Figure 4:
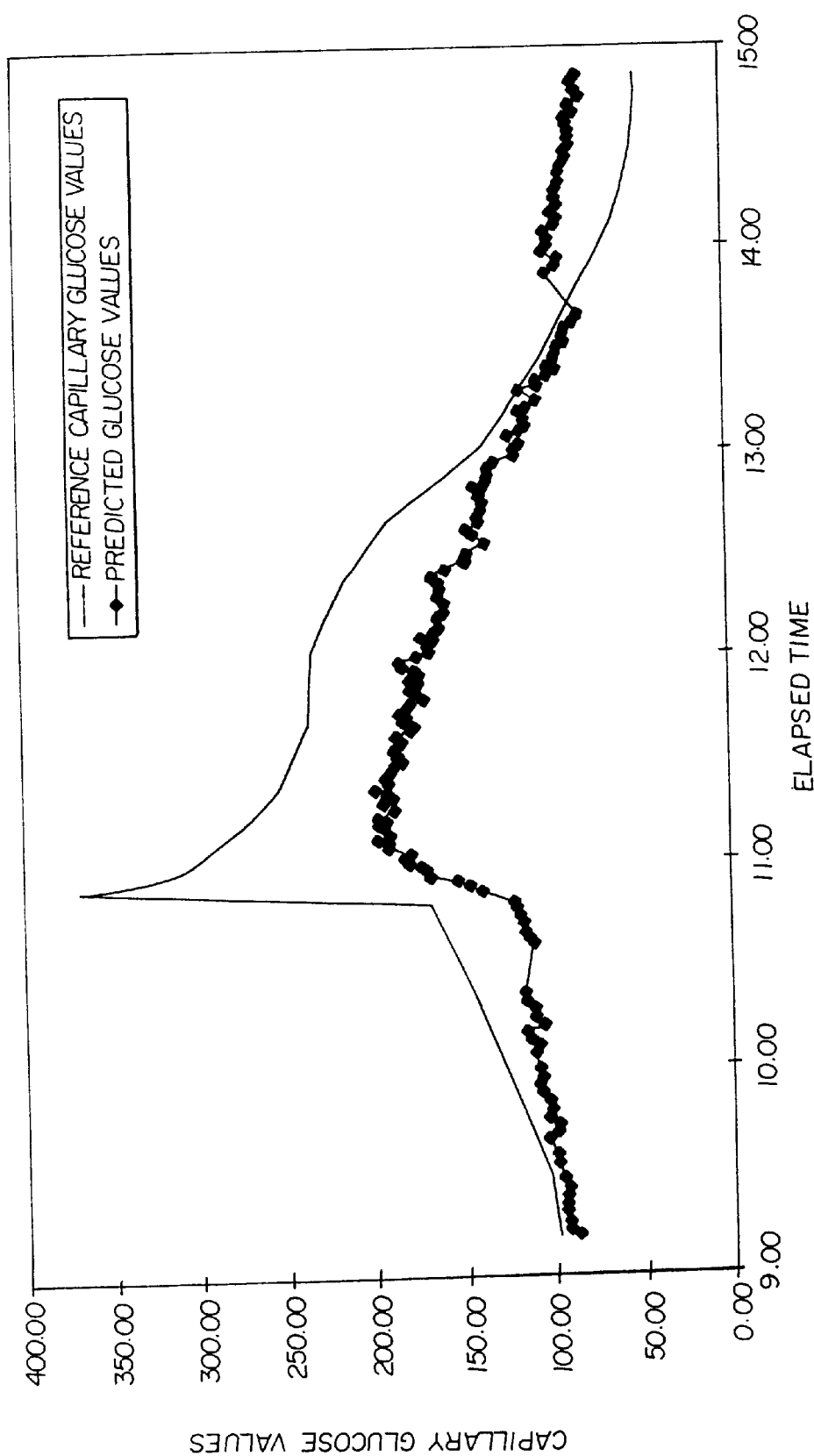
FIG. 4 is a graphical representation of experimental data showing the lag time between serial capillary glucose concentrations versus non-invasive tissue glucose concentration without means for equilibrating the concentration of glucose between the vascular system and the tissue.
Figure 5:
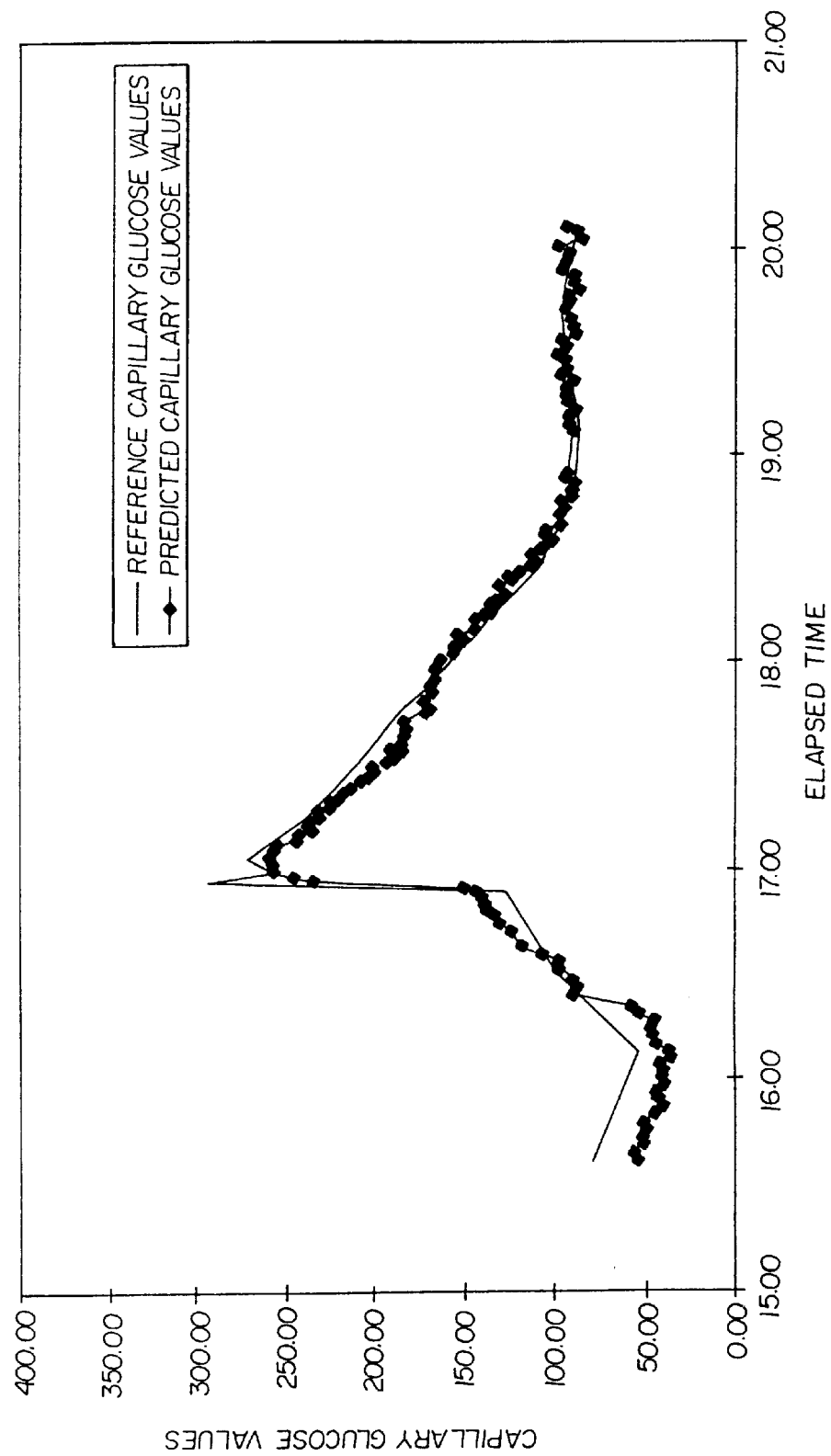
FIG. 5 is a graphical representation of experimental data showing the reduction or elimination of lag time when means for equilibrating the concentration of glucose between the vascular system and tissue is utilized.

The study was conducted by injecting a bolus of glucose via intravenous catheter into a non-diabetic patient while simultaneously measuring serial capillary glucose concentrations in the conventional manner and non-invasive "tissue" glucose concentration via near-infrared reflectance spectroscopy of the forearm. The reference capillary glucose values are indicated by the solid lines and spectroscopic measurements are shown as individual asterisks. The plot of FIG. 4 shows the results when the arm was unheated (at approximately 35° C.) and the plot of FIG. 5 shows the results of the identical experiment conducted with the arm locally heated to 40° C. Neither plot includes slope correction (correction factor for the fact that skin has intracellular water with low glucose content) so there is an inherent difference between blood glucose and tissue glucose concentration in water. However, the striking aspect of the two sets of measurements is how well the heated arm optical measurement follows the actual blood glucose concentration in terms of shape. In the unheated case there is a slow rise in the glucose measured optically, consistent with slow filling of the dermal and possibly the epidermal water volumes (since the blood flow is nominally constant through the study). Conversely, in the heated experiment, the maximum glucose concentration is reached by the second optical sample and there is no evidence of further filling or increase of the total skin glucose content. Thus, the lag has virtually disappeared with the implementation of local skin heating.

It is thus clear that the methodology of the present invention makes the replacement of some direct blood measurements (measurements that require blood to be drawn from the patient's veins, capillaries, or arteries) by non-invasive or minimally invasive means possible provided the equilibration rate can be increased sufficiently and sufficient time for equilibration is given prior to taking a reading. Improvement of the equilibration time of the dermis and blood will impact measurements of analytes that change quickly in the body. Blood components such as albumin or urea change relatively slowly in blood except for unique circumstances such as hemodialysis. As noted throughout this document, the preferred application of this technique is in the measurement of blood glucose concentration in diabetics. Given the time lag apparent between many of the alternative measurements and direct blood glucose concentration measurement, it is clear that insulin or caloric therapy based on these determinations are less than ideal. Accurate measurements with respect to time, including an equilibration period, provide detailed information that may be very useful in the non-invasive approach to diabetes management.

Example 3

As previously stated, in preferred embodiments of the present invention, the patient would place their "cold arm" in the non-invasive measurement device. Means for equilibrating glucose concentrations in fluid compartments would be activated. The monitor would make non-invasive measurements during the equilibration period. If the patient was at a stable glucose concentration and no equilibration between the tissue and blood was necessary, the non-invasive glucose reading would be constant. For example, the readings over the first three minutes would be approximately the same; however, if the patient's glucose was changing rapidly, or had been changing rapidly before the insertion, the non-invasive measurements would change rapidly over time due to the equilibration between the tissue and the blood.

To test this concept, a patient study was conducted where the patient's glucose was both varied and held constant. FIG.

6 depicts the results of these tests and is divided into three distinct sections: 1) period of constant glucose concentration; 2) period of increasing glucose concentration; and 3) period of decreasing glucose concentration. During each session, the patient's left and right arms were inserted into the measurement device. At the time of insertion into the device, the arm was in a "cold arm" condition. The arm remained inserted for twenty minutes during which time the arm was warmed to approximately 40° C.

Figure 6:
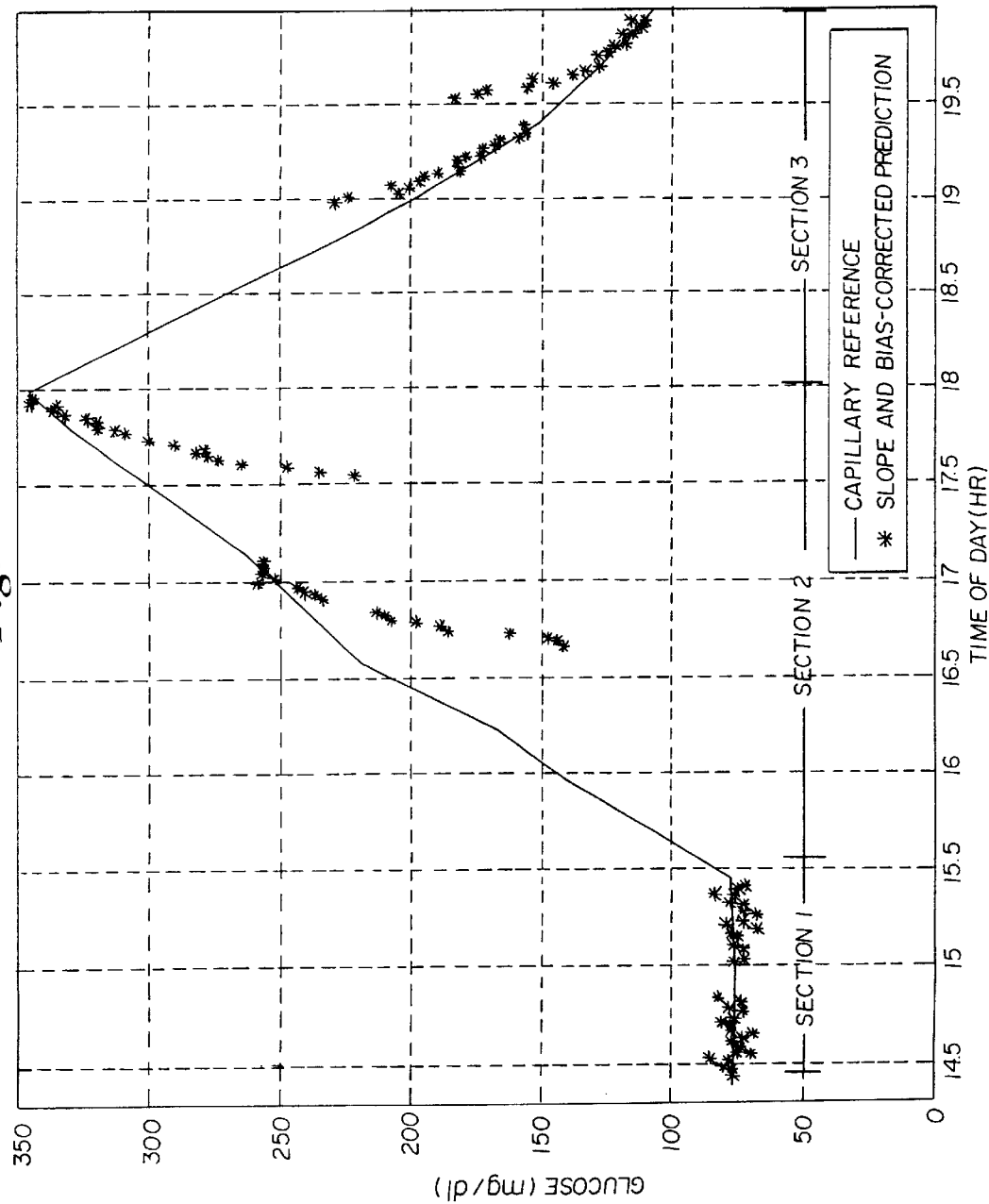
FIG. 6 is a graphical representation of experimental data showing the use of multiple overall tissue readings during equilibration to determine direction and rate of change of an analyte in blood.

In section 1 of FIG. 6, where the patient's glucose is stable, the non-invasive glucose measurements were relatively constant over the entire insertion period. Thus, both the "cold arm" and "warm arm" glucose predictions were similar. The blood glucose concentration was determined from a capillary blood sample and due to no significant changes in non-invasive measurements, one can conclude that the patient's glucose is and has been quite stable.

In section 2, the patient's glucose was increased at a rate of approximately 2 mg/dl per minute. Due to the fact that the arm is in its cold state, a difference between the tissue and the blood results. Upon insertion of the "cold arm" into the measurement device, the non-invasive measurement generates a reading that is below the actual blood value. As the arm warms up, the blood and tissue glucose values rapidly equilibrate. As the arm remains in the measurement device during this period of heating, multiple non-invasive tissue measurements can be made. As one can see from FIG. 6, the non-invasive measurements change rapidly and quickly equilibrate to the blood values. Examination of the right and left arm insertions during the period of increasing glucose concentration demonstrates that the direction and rate of change can be quantified in a general sense. The very rapid changes observed during the first few minutes would strongly suggest that the patient's glucose values had increased significantly over the preceding period.

In section 3, a period of decreasing glucose concentration, the ability to determine the direction, rate of change, and absolute value is still present. It is important to note that the same location on each arm was sampled during each section. Since the same location was used, the blood and tissue glucose concentrations of the left arm were equilibrated at the 17th hour. The tissue had approximately two hours to develop a condition of disequilibrium between the blood and the tissue. In the case of decreasing glucose concentration, the tissue will be at a higher glucose concentration than the blood. As observed in FIG. 6, the non-invasive prediction is above the blood concentration but again shows rapid equilibration. Again, the process of measuring a "cold arm" followed by warming of the arm enables the non-invasive measurement device to provide the patient with an absolute measure of glucose concentration as well as a measure of both the direction and rate of change of blood glucose concentration.

New characteristics and advantages of the invention covered by this document have been set forth in the foregoing description. It will be understood, however, that this disclosure is, in many respects, only illustrative. Changes may be made in details, particularly in matters of shape, size, and arrangement of parts, without exceeding the scope of the invention. The scope of the invention is, of course, defined in the language in which the appended claims are expressed.

What is claimed is:

1. A method for non-invasive spectroscopic measurement of analytes, said method comprising the steps of:

providing a means for irradiating tissue with infrared energy;

providing an output element, said output element operatively connected to a means for measuring a spectrum;

providing a means for increasing the rate of equilibration of analyte concentration between tissue compartments, said tissue compartments including vascular and non-vascular compartments;

activating said means for increasing the rate of equilibration of analyte concentration and allowing time for sufficient equilibration of analyte concentration between tissue compartments;

irradiating tissue including said compartments with said infrared energy so that there is differential absorption of said infrared energy in said tissue; and collecting infrared energy exiting said tissue through said output element and quantifying said infrared energy with said means for measuring a spectrum.

2. The method of claim 1, wherein sufficient time is allowed for approximately 100% equilibration.

3. The method of claim 1, wherein sufficient time is allowed for about 80% or greater equilibration.

4. The method of claim 1, wherein said activating step comprises heating said tissue compartments, and wherein sufficient time is allowed for the dermis temperature to increase.

5. The method of claim 1, wherein said activating step comprises heating said tissue compartments, and wherein at least approximately 2 minutes are allowed for equilibration of analyte concentration between tissue compartments.

6. The method of claim 1, wherein said activating step comprises heating said tissue compartments, and wherein at least approximately 3 minutes are allowed for equilibration of analyte concentration between tissue compartments.

7. The method of claim 1, wherein said activating step comprises applying a rubrifractant to said tissue, and wherein at least approximately 2 minutes are allowed for equilibration of analyte concentration between tissue compartments.

8. The method of claim 1, wherein said activating step comprises applying a rubrifractant to said tissue, and wherein at least approximately 3 minutes are allowed for equilibration of analyte concentration between tissue compartments.

9. The method of claim 1, wherein said means for increasing the rate of equilibration of analyte concentration comprises a heat source.

10. The method of claim 9, wherein said activating step comprises applying heat to said tissue utilizing said heat source.

11. The method of claim 9, wherein said heat source includes an infrared light.

12. The method of claim 10, wherein said heat is applied to the skin surface.

13. The method of claim 1, wherein said means for increasing the rate of equilibration of analyte concentration comprises a rubrifractant.

14. The method of claim 13, wherein said activating step comprises applying said rubrifractant to said tissue.

15. The method of claim 14, wherein said rubrifractant is applied to the skin surface.

16. The method of claim 1, wherein said means for irradiating said tissue includes an optical element and said means for increasing the rate of equilibration of analyte concentration includes said optical element.

17. The method of claim 16, wherein said step of activating said means for increasing the rate of equilibration of analyte concentration comprises heating said optical element.

18. The method of claim 17, wherein said step of activating said means for increasing the rate of equilibration of analyte concentration further comprises establishing contact between said optical element and said tissue said compartments.

19. The method of claim 1, further comprising irradiating said tissue compartments before or at the time of activating said means for increasing the rate of equilibration of analyte concentration, and collecting infrared energy exiting said tissue through said output element and quantifying said infrared energy with said spectrum analyzer.

20. The method of claim 1, further comprising collecting multiple readings of analyte concentration during said time for sufficient equilibration by multiple measurements of infrared energy exiting said tissue through said output element and multiple quantification of said infrared energy with said means for measuring a spectrum.

21. The method of claim 20, further comprising comparing said multiple readings to determine the degree of equilibration.

22. The method of claim 20, further comprising comparing said multiple readings to determine direction of change of analyte concentration.

23. The method of claim 20, further comprising comparing said multiple readings to determine the rate of change of analyte concentration.

24. A method for determining the direction of change of a concentration of an analyte in a testing period, said method comprising the steps of:
  providing a means for analyzing a concentration of said analyte in human fluid;
  providing a means for increasing the rate of equilibration of the analyte concentration between a vascular fluid compartment and a non-vascular fluid compartment;
  activating said means for increasing the rate of equilibration of the analyte concentration and taking multiple readings of said analyte concentration; and
  comparing said multiple readings to determine the direction of change of said analyte in said human fluid.

25. The method of claim 24, wherein said human fluid includes interstitial fluid.

26. The method of claim 24, wherein said human fluid includes such fluids found in human tissue.

27. The method of claim 24, wherein said means for analyzing said analyte concentration includes a non-invasive infrared spectrographic analyzer.

28. The method of claim 24, wherein said means for analyzing said analyte includes analysis of an interstitial fluid sample.

29. A method for non-invasive spectroscopic analysis of analytes, said method comprising the steps of:
  providing a means for irradiating tissue with infrared energy;
  providing an output element, said output element operatively connected to a means for measuring a spectrum;
  providing a means for reducing analyte concentration mismatches between the vascular fluid compartment and said tissue fluid compartments;
  applying said means to said tissue and allowing sufficient time for reduction of said concentration mismatch;
  irradiating said tissue with said infrared energy so that there is differential absorption of said infrared energy in said tissue; and
  collecting infrared energy exiting said tissue through said output element and quantifying said infrared energy with said means for measuring a spectrum.

30. The method of claim 29, wherein said means for reducing analyte concentration mismatches includes a rubrifractant compound, and said applying step comprises applying said rubrifractant compound to said tissue.

31. The method of claim 30, wherein said rubrifractant compound is selected from the group consisting of: nicotinic acid, methyl nicotinamide, minoxidil, nitroglycerin, histamine, menthol, capsaicin and mixtures thereof.

32. A method for non-invasive spectroscopic analysis of analytes in blood within a vascular system through analysis of tissue thereof, said method comprising the steps of:
  providing a means for irradiating said tissue with infrared energy;
  providing an output element, said output element operatively connected to a spectrum analyzer;
  providing an index-matching compound, said index-matching compound conforming to said surface of said tissue when applied thereto and having a refractive index closely matched to that of said tissue surface; disposing a quantity of said compound between said output element and said tissue surface to couple said output element to said tissue surface and said analytes in said tissue through said index-matching compound;
  providing means for equilibrating the concentration of said analyte between said vascular system and said tissue;
  activating said means for equilibrating the concentration of said analyte and allowing time for sufficient equilibration of analyte concentration between said vascular system and said tissue;
irradiating said tissue with said infrared energy so that there is differential absorption of said infrared energy in said tissue; and
  collecting infrared energy exiting said tissue through said output element as coupled to said tissue surface through said index-matching compound and quantifying said infrared energy with said spectrum analyzer.

33. The method of claim 32, wherein said means for equilibrating the concentration of said analyte between said vascular system and said tissue comprises means for heating said vascularized tissue to a temperature above skin temperature and for sufficient time to increase the rate of blood flow.

34. The method of claim 33, wherein said step of activating said means for equilibrating the concentration of said analyte comprises heating said tissue.

35. The method of claim 34, wherein said means for irradiating said tissue includes an optical element and said means for heating said tissue includes said optical element.

36. The method of claim 35, wherein said step of heating said tissue comprises heating said optical element.

37. The method of claim 35, wherein said optical element is maintained at a temperature between about 38° C. and about 42° C.

38. An apparatus for non-invasive measurement of an analyte in human tissue, said human tissue including multiple fluid compartments having a concentration of said analyte disposed therein, said apparatus comprising:
  a source of at least three wavelengths of light, said wavelengths being in the range of 300 to 2500 nm;
  an input sensor element for directing said light into said tissue and output sensor element for collecting at least a portion of the non-absorbed light from said tissue;
  means for increasing the rate of equilibration of the concentration of said analyte between said multiple fluid compartments until a sufficient amount of said equilibration has occurred;

means for measuring and processing the collected portion of the non-absorbed light from said tissue after equilibration; and, means for indicating a value of said analyte concentration.

39. A method for non-invasive spectroscopic measurement of analytes, said method comprising the steps of:

providing a means for irradiating tissue with infrared energy;

providing an output element, said output element operatively connected to a spectrum analyzer;

providing a means for increasing the rate of equilibration of analyte concentration between tissue compartments, said tissue compartments including vascular and dermal interstitial fluid compartments;

activating said means for increasing the rate of equilibration of analyte concentration and allowing time for sufficient equilibration of analyte concentration between tissue compartments;

irradiating said tissue adjacent said dermal interstitial fluid compartment with said infrared energy so that there is differential absorption of said infrared energy in said tissue adjacent said dermal interstitial fluid compartment; and collecting infrared energy exiting said tissue adjacent said dermal interstitial fluid compartment through said output element and quantifying said infrared energy with said spectrum analyzer.

* * * * *